(12) United States Patent
Ueno

(10) Patent No.: US 10,537,721 B2
(45) Date of Patent: Jan. 21, 2020

(54) MICRONEEDLE UNIT AND MICRONEEDLE CONTAINER

(71) Applicant: TOPPAN PRINTING CO., LTD., Taito-ku (JP)

(72) Inventor: Hisami Ueno, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 269 days.

(21) Appl. No.: 15/241,788

(22) Filed: Aug. 19, 2016

(65) Prior Publication Data

US 2016/0354591 A1 Dec. 8, 2016

Related U.S. Application Data

(63) Continuation of application No. PCT/JP2015/055979, filed on Feb. 27, 2015.

(30) Foreign Application Priority Data

Feb. 27, 2014 (JP) ................................. 2014-036948

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01)

(58) Field of Classification Search
CPC ...... A61M 37/0015; A61M 2037/0023; A61M 2037/0053; A61M 5/002; A61M 2205/21; A61M 2205/215; A61M 2209/06
See application file for complete search history.

(56) References Cited

U.S. PATENT DOCUMENTS

2003/0135161 A1 7/2003 Fleming et al.
2005/0187521 A1 8/2005 Fleming et al.
(Continued)

FOREIGN PATENT DOCUMENTS

JP 2005-514179 A 5/2005
JP 2013-13558 A 1/2013

OTHER PUBLICATIONS

International Search Report dated Jun. 2, 2015 in PCT/JP2015/055979, filed Feb. 27, 2015.

*Primary Examiner* — Nathan R Price
*Assistant Examiner* — Tasnim M Ahmed
(74) *Attorney, Agent, or Firm* — Oblon, McClelland, Maier & Neustadt, L.L.P.

(57) ABSTRACT

A microneedle container includes a housing that houses a microneedle and a cover that covers the microneedle. The microneedle includes a base having a first surface on which a projection is formed and a second surface supported by a supporting portion of the housing. The base has an abutted portion on the first surface where the projection is not formed, and the cover has an abutment portion that faces the abutted portion, and a facing portion that faces the projection. A distance between the abutment portion and the facing portion is larger than that between the abutted portion and a distal end of the projection in a direction in which the projection extends. A distance between the abutment portion and the supporting portion is smaller than a sum of a distance between the abutted portion and the second surface and a distance between the abutted portion and the distal end.

20 Claims, 15 Drawing Sheets

(56) References Cited

U.S. PATENT DOCUMENTS

2006/0036208 A1\* 2/2006 Burnett ............ A61M 5/14276
  604/9
2013/0218084 A1\* 8/2013 Tamaru ............ A61M 37/0015
  604/173

\* cited by examiner

MICRONEEDLE UNIT AND MICRONEEDLE CONTAINER

CROSS-REFERENCE TO RELATED APPLICATIONS

The present application is a continuation of International Application No. PCT/JP2015/055979, filed Feb. 27, 2015, which is based upon and claims the benefits of priority to Japanese Application No. 2014-036948, filed Feb. 27, 2014. The entire contents of these applications are incorporated herein by reference.

BACKGROUND OF THE INVENTION

Field of the Invention

The technique of the present disclosure relates to a microneedle unit having a microneedle and a microneedle container, and a microneedle container that houses the microneedle.

Discussion of the Background

Transdermal absorption is a method commonly used for painless drug administration, which allows for administration of a drug by delivering a drug into the body by osmosis through the skin. In the transdermal absorption method, attention has been drawn to a technique of administration by using a microneedle that forms pores in the skin so that a drug of low delivery rate can be administered through the skin into the body through the pores by osmosis.

The microneedle includes a projection, a portion to be pierced into the skin, which is a fine structure. Accordingly, for example as described in PTL 1, the microneedle is shipped or stored in the state of being contained in a container that houses the microneedle.

PTL 1: JP-A-2013-13558

SUMMARY OF THE INVENTION

According to one aspect of the present invention, a microneedle unit includes a microneedle, and a microneedle container having a housing that houses the microneedle and a cover that covers the microneedle housed in the housing. The microneedle includes a base having a first surface on which a projection is formed and a second surface which is opposite to the first surface and supported by a supporting portion of the housing. The base has an abutted portion on the first surface where the projection is not formed. The cover has an abutment portion that faces the abutted portion, and a facing portion that faces the projection. The base and the cover are structured such that a distance between the abutment portion and the facing portion is larger than a distance between the abutted portion and a distal end of the projection in a direction in which the projection extends, and that a distance between the abutment portion and the supporting portion is smaller than a sum of a distance between the abutted portion and the second surface and a distance between the abutted portion and the distal end of the projection in the extending direction.

According to another aspect of the present invention, a microneedle container includes a container body including a housing structured to house a microneedle and a cover structured to cover the microneedle. The cover has an abutment portion positioned to face an abutted portion of the microneedle, and a facing portion positioned to face a projection of the microneedle, and the cover is structured such that a distance between the abutment portion and the facing portion is larger than a distance between the abutted portion and a distal end of the projection in a direction in which the projection extends.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
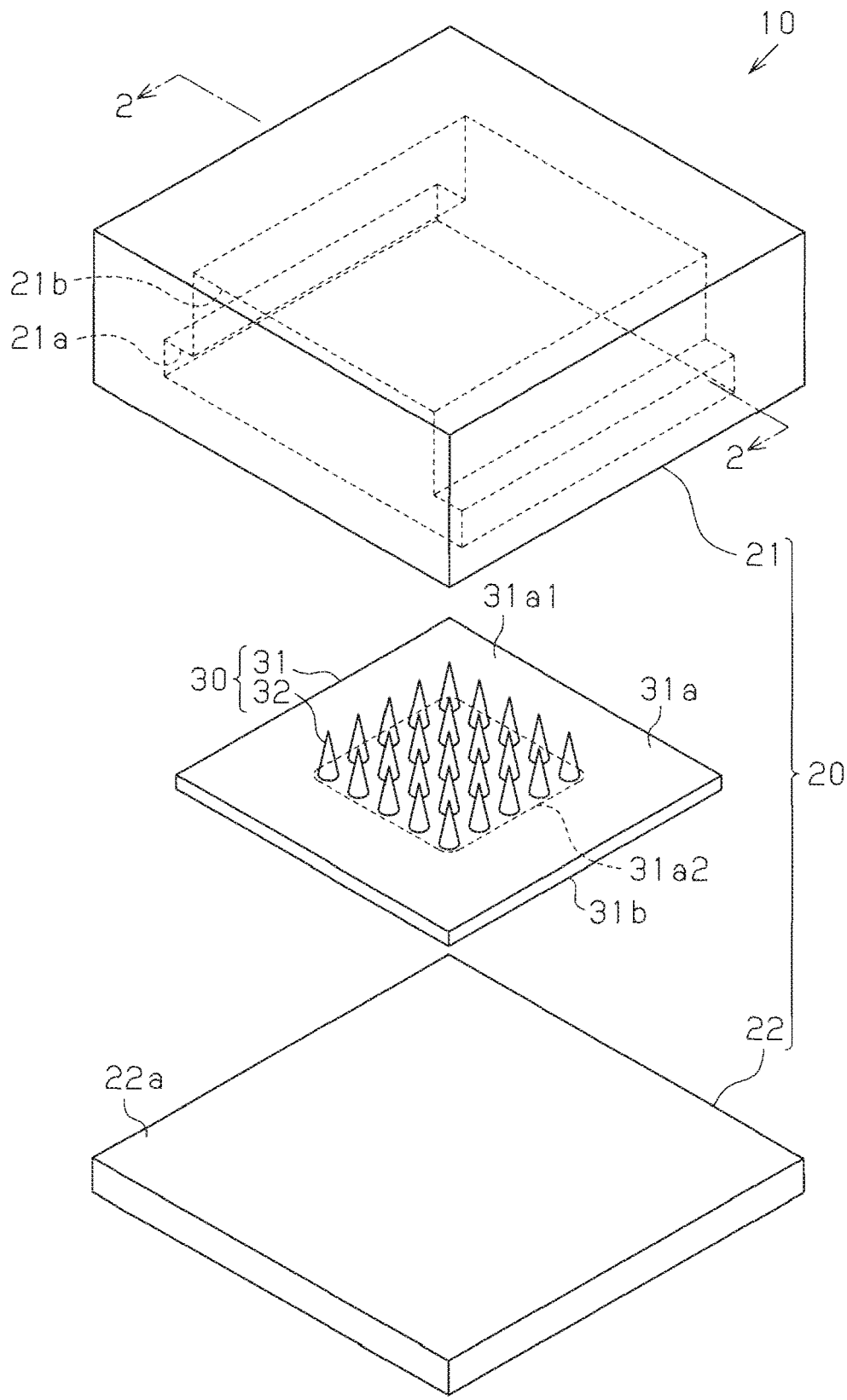
FIG. 1 is an exploded perspective view which shows an exploded perspective configuration of a microneedle unit according to a first embodiment of the present disclosure.

The embodiments will now be described with reference to the accompanying drawings, wherein like reference numerals designate corresponding or identical elements throughout the various drawings.

<First Embodiment>

With reference to FIGS. 1 to 7, a first embodiment of a microneedle unit and a microneedle container according to the technique of the present disclosure will be described. A configuration of a microneedle unit, and a configuration of a microneedle will be each described below.

<Configuration of Microneedle Unit>

Figure 2:
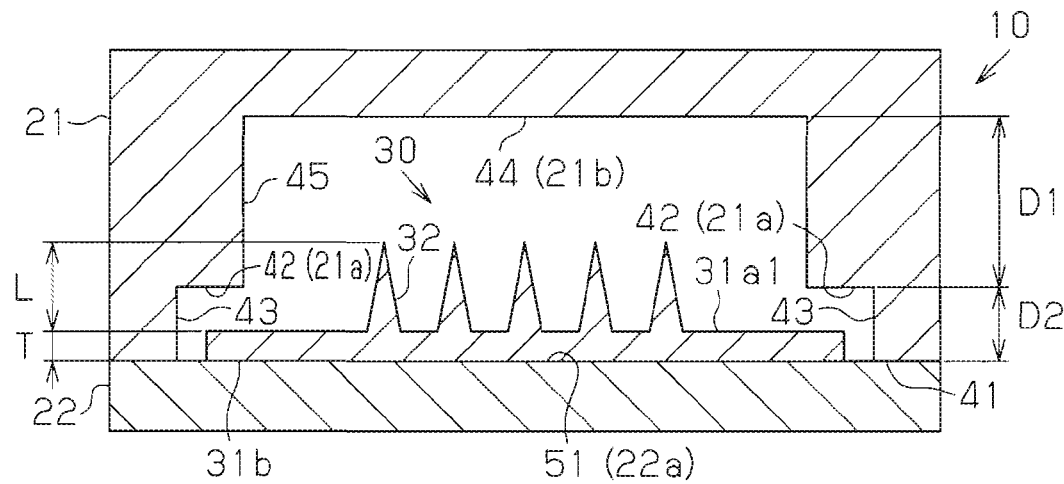
FIG. 2 is a cross sectional view, taken along the line 2-2 of FIG. 1, which shows a cross sectional configuration of the microneedle unit according to the first embodiment.
Figure 3:
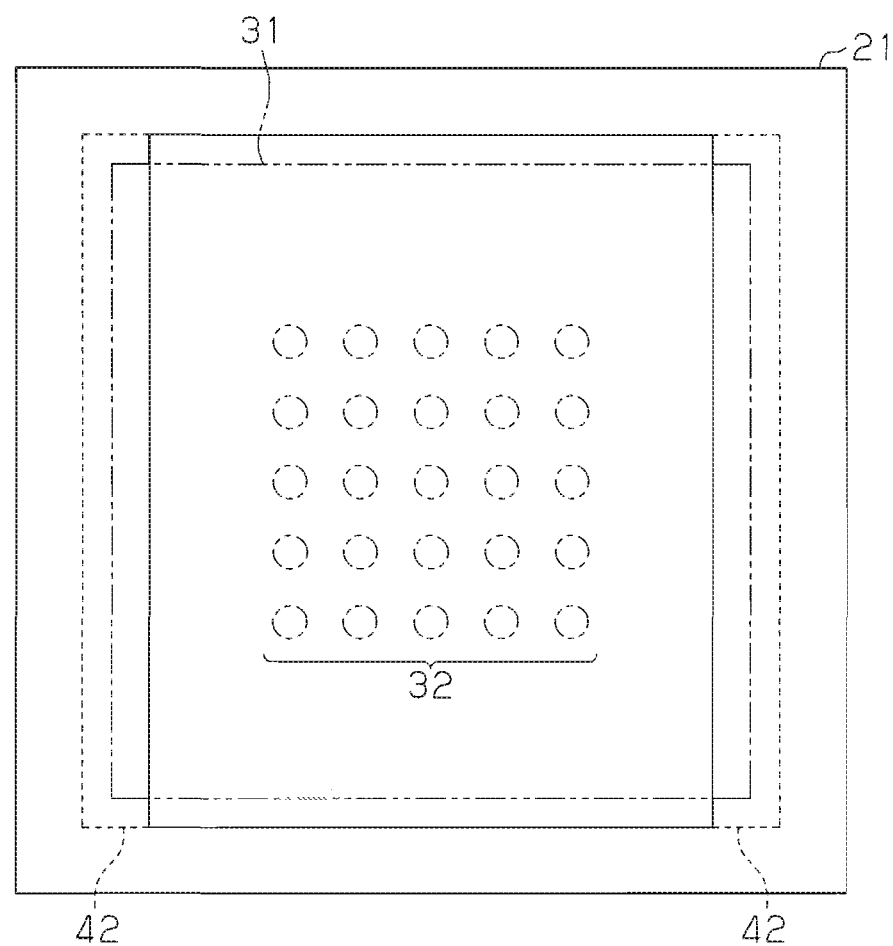
FIG. 3 is a plan view which shows a plan configuration of the cover as seen from the wall surface having a cover facing surface in the microneedle unit according to the first embodiment.

With reference to FIGS. 1 to 5, a configuration of a microneedle unit will be described. In the following description, a plurality of different examples of the microneedle unit of the first embodiment will be described. Further, FIG. 3 is a plan view that shows a plan configuration of the cover as seen from the wall surface having the cover facing surface of the microneedle unit. In FIG. 3, for the convenience of explanation of the arrangement of the abutment surface of the cover, the wall surface having the cover facing surface is not illustrated, and the abutment surface formed on the cover is illustrated by the dotted line.

As shown in FIG. 1, a microneedle unit 10 includes a microneedle container 20 and a microneedle 30.

The microneedle 30 includes a plate-shaped base 31 and projections 32. Of the surfaces of the base 31, a surface on which the projections 32 are located is a projection forming surface 31a, and a surface opposite to the projection forming surface 31a is a supported surface 31b. The projection forming surface 31a includes an abutted section 31a1 which is a portion in which the projections 32 are not located, and a projection forming section 31a2 which is a portion in which the projections 32 are located. Although the projection forming surface 31a includes, for example, a plurality of projection forming sections 31a2, the projection forming surface 31a may have a single projection forming section 31a2.

The microneedle container 20 includes a cover 21 and a housing 22. The cover 21 includes an abutment section 21a that faces the abutted section 31a1 of the base 31, and a facing section 21b that faces the projections 32. The housing 22 includes a supporting section 22a that supports the supported surface 31b of the base 31.

The projection 32 extends in a direction from the base 31 toward the facing section 21b, which is an extending direction, and the distance between the abutment section 21a and the facing section 21b in the extending direction is larger than a length of the projection 32. Furthermore, the distance between the abutment section 21a and the supporting section 22a is smaller than the sum of a thickness of the base 31 in the extending direction and the length of the projection 32.

That is, in the microneedle container 20, the distance between the abutment section 21a and the facing section 21b in the extending direction is larger than the distance between the abutted section 31a1 and the distal end of the projection 32. Furthermore, the distance between the abutment section 21a and the supporting section 22a is smaller than the sum of the distance between the abutted section 31a1 and the supported surface 31b and the distance between the abutted section 31a1 and the distal end of the projection 32.

As shown in FIG. 2, the distance between the abutment section 21a and the facing section 21b in the extending direction is a facing distance D1, and the facing distance D1 is larger than a length L of the projection 32. The cover 21 is formed, for example, in a rectangular tubular shape with one of two tubular ends closed. Alternatively, the cover 21 may be formed in a hemisphere or elliptical hemisphere shape. When the cover 21 is formed in a tubular shape, the tubular shape may be a polygonal tubular shape or a circular tubular shape.

The cover 21 has a stepped inner surface, and the inner surface includes an abutment surface 42, an abutment side surface 43, a cover facing surface 44 and a facing side surface 45. The abutment surface 42 is a surface which forms a step from a cover opening end 41, which is one of two tubular ends and open to the housing 22, and the abutment side surface 43 is a surface that connects the cover opening end 41 and the abutment surface 42. The cover facing surface 44 is a surface which forms a step from the abutment surface 42, and the facing side surface 45 is a surface that connects the abutment surface 42 and the cover facing surface 44. The abutment surface 42 is an example of the abutment section 21a, and the cover facing surface 44 includes the facing section 21b as part of the cover facing surface 44.

The facing distance D1, which is the distance between the abutment surface 42 and the cover facing surface 44 of the inner surface of the cover 21, is larger than the length L of the projection 32 in the extending direction. As a consequence, the distal end of the projection 32 does not come into contact with the cover facing surface 44 when the abutment surface 42 abuts the abutted section 31a1 of the base 31. Accordingly, the distal end of the projection 32 is prevented from being deformed into a shape inappropriate for piercing into the target, for example, a shape of the distal end of the projection 32 bent into a direction intersecting with the extending direction.

The housing 22 may have any configuration as long as it includes the supporting section 22a that supports the supported surface 31b of the base 31, and the housing 22 is, for example, formed in a plate shape that closes the cover opening end 41 of the cover 21. The plate shape of the housing 22 may be rectangular plate shape, a disc shape, a flat plate shape or a curved plate shape. A surface which is one of the surfaces of the housing 22 faces the microneedle 30 is a housing facing surface 51, and the housing facing surface 51 includes the supporting section 22a.

As shown in FIG. 3, the abutment surfaces 42 are located on part of the perimeter on the inner surface of the cover 21. The abutment surfaces 42 are provided to overhang from each of two opposing surfaces on the inner surface of the cover 21. Each of two abutment surfaces 42 are entirely located on each surface in a direction perpendicular to a direction in which the aforementioned two opposing surfaces oppose to each other. At a portion of the inner surface of the cover 21 in which the abutment surfaces 42 are not located in the perimeter direction, a side surface which connects the cover opening end 41 and the cover facing surface 44 is located.

Further, each of the two abutment surfaces 42 may overhang from part of the surface from which the abutment surfaces 42 overhang. Positions at which each of the two abutment surfaces 42 are formed may or may not oppose to each other in a direction in which each of the overhanging surfaces of the abutment surfaces 42 oppose to each other. Alternatively, on the inner surface of the cover 21, the abutment surfaces 42 may be located on the entire perimeter of the cover 21.

As shown in FIG. 2, a distance between the abutment surface 42 of the cover 21 and the housing facing surface 51 of the housing 22 with the base 31 interposed therebetween is a nipping distance D2, and the nipping distance D2 is smaller than the sum of the length L of the projection 32 of the microneedle 30 and a thickness T of the base 31. As a consequence, the projection 32 does not come into contact with the inner surface of the microneedle container 20 when the base 31 is displaced in the thickness direction. Accordingly, the projection 32 of the microneedle 30 is prevented from being deformed when the microneedle container 20 is subject to vibration in the thickness direction of the base 31.

Figure 4:
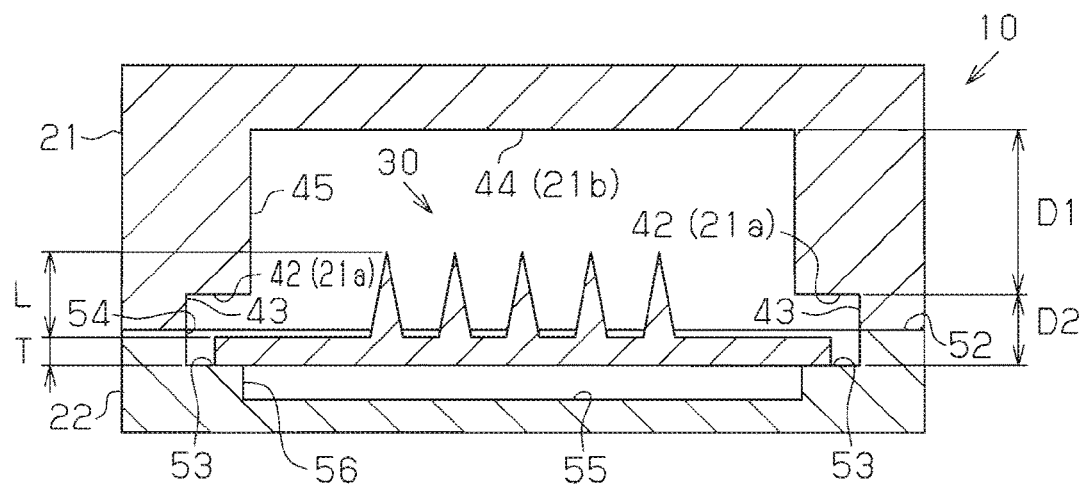
FIG. 4 is a cross sectional view which shows a cross sectional configuration of the microneedle unit according to the first embodiment.

As shown in FIG. 4, the housing 22 may be formed in a rectangular tubular shape with one of two tubular ends closed. Alternatively, the housing 22 may be formed in a hemisphere or elliptical hemisphere shape. When the housing 22 is in a tubular shape, the tubular shape may be a polygonal tubular shape or a circular tubular shape. The housing 22 has a stepped inner surface, and the inner surface includes a supporting surface 53, a supporting side surface 54, a housing facing surface 55 and a housing side surface 56. The supporting surface 53 is a surface which forms a step from a housing opening end 52, which is one of two tubular ends and open to the cover 21, and the supporting side surface 54 is a surface that connects the housing opening end 52 and the supporting surface 53. The housing facing surface 55 is a surface which forms a step from the supporting surface 53, and the housing side surface 56 is a surface that connects the supporting surface 53 and the housing facing surface 55. The supporting surface 53 is one example of the supporting section 22a.

Similarly to the abutment surface 42 of the cover 21, the supporting surfaces 53 are located on part of the perimeter on the inner surface of the housing 22. The supporting surfaces 53 are provided to overhang from each of two opposing surfaces on the inner surface of the housing 22. Each of two supporting surfaces 53 are entirely located on each surface in a direction perpendicular to a direction in which the aforementioned two opposing surfaces oppose to each other. At a portion of the inner surface of the housing 22 in which the supporting surfaces 53 are not located in the perimeter direction, a side surface which connects the housing opening end 52 and the housing facing surface 55 is located.

Further, each of the two supporting surfaces 53 may overhang from part of the surface from which the supporting surfaces 53 overhang. Positions at which each of the two supporting surfaces 53 are formed may not oppose to each other in the opposing direction. Alternatively, on the inner surface of the housing 22, the supporting surfaces 53 may be located on the entire perimeter.

When the microneedle container 20 is assembled, the position of the abutment surface 42 of the cover 21 and the position of the supporting surface 53 of the housing 22 overlap each other in the stacking direction of the housing 22 and the cover 21. As a consequence, compared with the configuration in which two positions do not overlap each other, the microneedle container 20 more reliably stabilizes the position of the microneedle 30.

Figure 5:
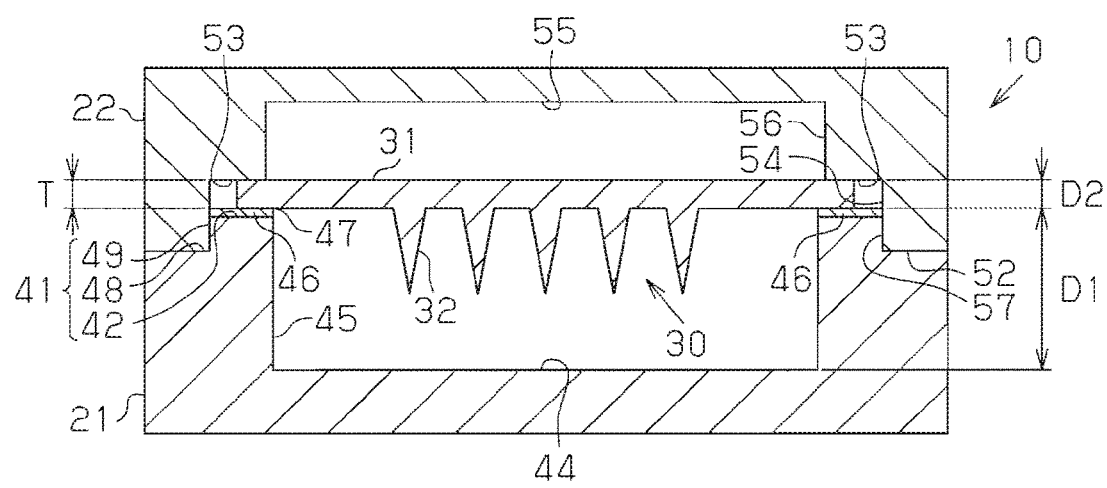
FIG. 5 is a cross sectional view which shows a cross sectional configuration of the microneedle unit according to the first embodiment.

As shown in FIG. 5, the nipping distance D2 may be equal to the thickness T of the base. That is, when the microneedle 30 is housed in the microneedle container 20, the abutment surface 42 and the supporting surface 53 are simultaneously in contact with the base 31.

An adhesive strength of the abutment surface 42 to the base 31 may be the same or different from an adhesive strength of the supporting surface 53 to the base 31. When the adhesive strength of the abutment surface 42 to the base 31 and the adhesive strength of the supporting surface 53 to the base 31 are different from each other, one of the cover 21 and the housing 22 more securely holds the microneedle 30, while the other less securely holds the microneedle 30 in the microneedle container 20. As a consequence, the microneedle 30 can be easily taken out.

When the adhesive strength of the abutment surface 42 to the base 31 and the adhesive strength of the supporting surface 53 to the base 31 are different from each other, the abutment surface 42 may have a higher adhesive strength to the base 31 than the adhesive strength of the supporting surface 53, or the supporting surface 53 may have a higher adhesive strength to the base 31 than the adhesive strength of the abutment surface 42. For example, as shown in FIG. 5, when the abutment surface 42 has a higher adhesive strength to the base 31 than the adhesive strength of the supporting surface 53, the cover 21 may only include a close-contact section 46 at least part of the portion that forms the abutment surface 42.

The close-contact section 46 may have a configuration less slippery to the base 31 than the supporting surface 53 is, or may be made of a forming material less slippery to the base 31 or more adhesive to the base 31. When the close-contact section 46 has a less slippery configuration to the base 31, the close-contact section 46 has, for example, a surface roughness larger than that of the supporting surface 53.

When the close-contact section 46 is made of a forming material less slippery to the base 31 or a forming material more adhesive to the base 31, examples of the forming material of the housing 22, which includes the supporting surface 53, include resin, hard brittle material, metal and ceramics. When the forming material is a resin, examples of the forming material include thermoplastic resin, UV-treatment resin and silicone resin. When the forming material is a thermoplastic resin, examples of the forming material include acrylic resin, polyethylene resin, polypropylene resin, polyacetal resin, polystyrene resin, polycarbonate resin and cyclic olefin copolymer. When the forming material is a hard brittle material, examples of the forming material include silicon, glass, quartz and the like. When the forming material is a metal, the forming materials include nickel, aluminum, stainless steel, brass and titanium. When the forming material is a ceramics, examples of the forming material include alumina, aluminum nitride and machinable ceramics.

When the forming material of the close-contact section 46 is a material less slippery to the base 31, the forming material of the close-contact section 46 is, for example, a silicone resin. When the forming material of the close-contact section 46 is a silicone resin, the forming material of the housing 22 is preferably any of the aforementioned materials other than a silicone resin. Alternatively, when the forming material of the housing 22 is a silicone resin, at least part of the supporting surface 53 is preferably made of a material more slippery to the base 31 than a silicone resin is.

When the forming material of the close-contact section 46 is a more adhesive material than the forming material of the supporting surface 53, the forming material of the close-contact section 46 is, for example, a urethane resin. When the forming material of the close-contact section 46 is a urethane resin, the forming material of the housing 22 may be any of the aforementioned materials.

The forming material of the cover 21 may be the same or different from the forming material of the housing 22. For the purpose of reducing the number of forming materials of the microneedle container 20, the forming material of the cover 21 is preferably the same as that of the housing 22.

Furthermore, when the supporting surface 53 has the adhesive strength to the base 31 higher than the adhesive strength of the abutment surface 42, the forming material of the cover 21, which includes the abutment surface 42, may be any of the above forming materials of the housing 22, and at least part of the supporting surface 53 may have any of the above configurations of the close-contact section 46.

As shown in FIG. 5, when each of the abutment surface 42 and supporting surface 53 are in contact with the base 31, and one of the abutment surface 42 and the supporting surface 53, for example, the abutment surface 42, has the close-contact section 46 having the adhesive strength to the base 31 higher than the adhesive strength of the supporting surface 53, the following configuration is preferable.

That is, the cover 21, which is an example of the close contact member, is a recess-shaped member and includes the cover opening end 41 that surrounds an opening 47. The cover opening end 41 includes the abutment surface 42, a contact surface 48 that forms a step from the abutment surface 42, and an opening side surface 49 that connects the abutment surface 42 and the contact surface 48. In the cover opening end 41, the abutment surface 42 is located inside the contact surface 48, and the abutment surface 42 protrudes from the contact surface 48 in the extending direction. The abutment surface 42 may be located on the entire cover opening end 41 in the perimeter direction, or may be located on part of the cover opening end 41 in the perimeter direction. When the abutment surface 42 is located on part of the cover opening end 41 in the perimeter direction, a surface flush with the contact surface 48 may be located in the cover opening end 41 at a position inside the contact surface 48 and where the abutment surface 42 is not located.

When the abutment surface 42 is located on part of the cover opening end 41 in the perimeter direction, two or more abutment surfaces 42 are preferably located. When two or more abutment surfaces 42 are located, a plurality of abutment surfaces 42 may be positioned with an equal interval, or may be unevenly positioned in the perimeter direction.

When the microneedle container 20 is opened, the microneedle 30 is easily held on the close-contact section 46, and the microneedle 30 on the close-contact section 46 protrudes from the contact surface 48 in the extending direction. Accordingly, the microneedle 30 is easily taken out from the cover 21.

The inner surface of the cover 21 includes the cover facing surface 44 that forms a step from the abutment surface 42, and the facing side surface 45 that connects the abutment surface 42 and the cover facing surface 44. Furthermore, when the abutment surface 42 is located on part of the cover opening end 41 in the perimeter direction, the facing side surface 45 connects the surface flush with the contact surface 48 and the cover facing surface 44 at a position where the abutment surface 42 is not located.

The housing 22 is a recess-shaped member similarly to the cover 21, and the housing opening end 52 that surrounds the opening 57 is an example of the contact section that is in contact with the contact surface 48 of the cover 21. When the contact surface 48 of the cover 21 and the housing opening end 52 of the housing 22 are in contact with each other, the nipping distance D2 is equal to the thickness T of the microneedle 30.

<Configuration of Microneedle>

Figure 6:
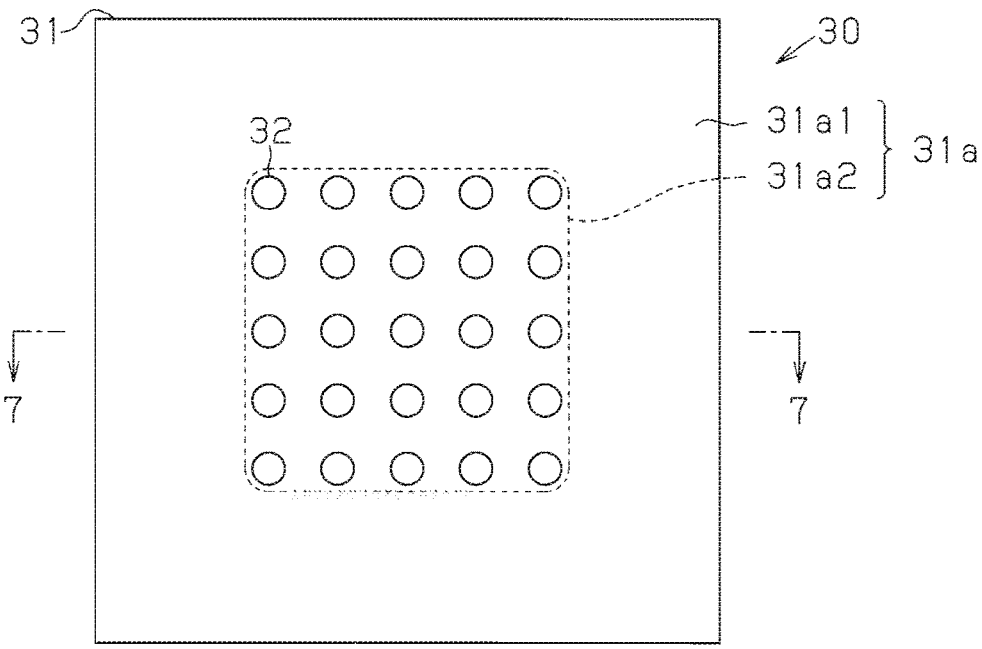
FIG. 6 is a top view which shows a top view of a projection forming surface of the microneedle according to the first embodiment.
Figure 7:
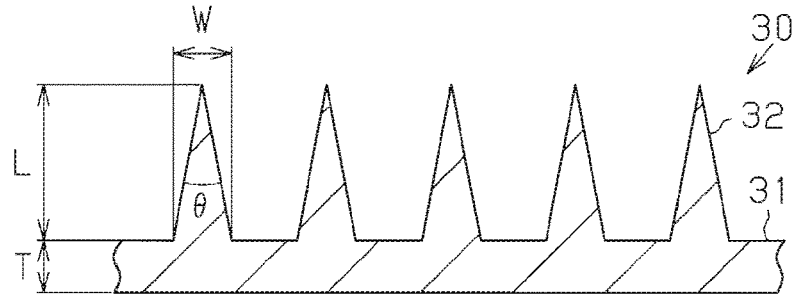
FIG. 7 is a partial cross sectional view, taken along the line 7-7 of FIG. 6, which shows a partial cross sectional configuration of the microneedle.

With reference to FIGS. 6 and 7, a configuration of the microneedle 30 housed in the microneedle container 20 will be described in detail.

As shown in FIG. 6, the microneedle 30 includes the base 31 and projections 32 which protrude from the projection forming surface 31a of the base 31 in the extending direction. A plurality of projections 32 of the microneedle 30 are arranged in matrix. However, the projections 32 may also be arranged in a predetermined regular pattern, such as a close-packed pattern or concentric pattern. Alternatively, a plurality of projections 32 may be irregularly provided.

The projection 32 is formed, for example, in a pyramid shape. However, the projection 32 may also be formed in a columnar shape or a frustum shape. When the projection 32 has a pyramid shape, the pyramid shape may be a cone shape or a polygonal pyramid shape. When the projection 32 has a columnar shape, the columnar shape may be a circular columnar shape or a polygonal columnar shape. When the projection 32 has a frustum shape, the frustum shape may be a truncated cone shape or a truncated polygonal shape. The plurality of projections 32 may have the shapes that are the same or different from each other.

The projections 32 may have two or more different shapes in the extending direction. For example, the projections 32 may be in a pencil-like shape formed of a combination of a columnar shape and a frustum shape provided in this order from the base 31 of the microneedle 30. Further, when the projections 32 have two or more different shapes, the projections 32 may have at least two or more shapes of a group of the shapes described above. The outer surface of the projection 32 may have a twist or a step.

The shapes and dimensions of the projection 32 may be appropriately selected depending on the applications of the microneedle 30. For example, the applications of the microneedle 30 include promoting absorption of a delivery substance to be delivered into the body of target via the skin or removing a substance in the body to the outside via the skin.

Alternatively, the shapes and dimensions of the projection 32 may be selected in view of the piercing properties into the skin. For example, when the hole formed by the projection 32 has a depth that passes through the stratum corneum and does not reach the nerve plexus, a delivery substance or a cosmetic composition is delivered deeper than the stratum corneum of the skin. Since the hole formed in the stratum corneum is closed with the elapse of time, the delivery substance or cosmetic composition delivered deeper than the stratum corneum is held in the body in a state protected from the outside by the stratum corneum.

Accordingly, the delivery substance or cosmetic composition is prevented from being excreted from the skin through metabolism of the stratum corneum or the cleansing of the skin during skin care. For example, when a cosmetic composition is applied, the make-up on the skin by the cosmetic composition is kept for a long period of time compared with the case where the hole has a depth within the stratum corneum.

For example, when the hole formed by the projection 32 has a depth within the stratum corneum, a delivery substance or a cosmetic composition remains in the stratum corneum. Since the stratum corneum is repeatedly generated by the metabolism, the delivery substance or cosmetic composition in the stratum corneum is excreted with the elapse of time. Accordingly, the make-up on the skin by the cosmetic composition and the delivery substance delivered in the skin can be easily removed by cleansing of the skin or peeling of the skin.

With reference to FIG. 7, the relationship between the piercing properties of the projection 32 into the skin and the length of the projection 32 will be described.

As shown in FIG. 7, when the hole formed by the projection 32 has a depth that passes through the stratum corneum and does not reach the nerve plexus, the length L of the projection 32 is preferably in the range between 200 µm or more and 700 µm or less, more preferably in the range between 200 µm or more and 500 µm or less. Further more preferably, the length L of the projection 32 is in the range between 200 µm or more and 300 µm or less.

When the hole formed by the projection 32 has a depth within the stratum corneum, the length L of the projection 32 is preferably in the range between 30 µm or more and 300 µm or less, more preferably, in the range between 30 µm or more and 250 µm or less. Further more preferably, the length L of the projection 32 is in the range between 30 µm or more and 40 µm or less.

When the microneedle 30 includes a plurality of projections 32, the lengths of the projections 32 may be the same or different from each other. For example, when the lengths of the projections 32 are different from each other, the projections 32 forming the outer perimeter of the projection forming section 31a2 out of the plurality of projections 32 arranged in a predetermined array may have the length L larger than the length L of the other projections 32. With this configuration, each of the plurality of projections 32 can be in contact with the target when the target to be pierced by the microneedle 30 is a curved surface.

Alternatively, when the lengths of the projections 32 are different from each other, the projections 32 forming the outer perimeter of the projection forming section 31a2 out of the plurality of projections 32 arranged in a predetermined array may have the length L smaller than the length L of the other projections 32. The projections 32 located on the outer perimeter of the projection forming section 31a2 out of the plurality of projections 32 are more easily deformed than the projections 32 located in the other positions in the projection forming section 31a2. In this regard, when the projection 32 located on the outer perimeter of the projection forming section 31a2 has the length L smaller than the length L of the other projections 32, the projection 32 located on the outer perimeter of the projection forming section 31a2 may have an increased mechanical strength. As a result, the projections 32 located on the outer perimeter of the projection forming section 31a2 are less easily deformed.

Further, when the lengths of the projections 32 are different from each other, the facing distance D1 described above may be larger than the length L of the projection 32 having the maximum length among the plurality of projections 32 in the extending direction.

Preferably, the projection 32 has a width W in the range between 1 µm or more and 300 µm or less. The width W of the projection 32 is preferably selected within the above range, considering the depth that the hole formed by the projection 32 pierced into the target reaches in the skin.

The width W of the projection 32 is a maximum length of the projection 32 on the projection forming surface 31a in the projection view projected on the base 31 when the projection 32 is projected in parallel with the projection forming surface 31a of the base 31. For example, when the projection 32 has a cone shape, the width W is a diameter of the circle of the base end of the projection 32 which is in contact with the projection forming surface 31a of the base 31. When the projection 32 has a regular square pyramid shape, the width W is a diagonal length of the square of the base end of the projection 32. When the projection 32 has a columnar shape, the width W is a diameter of the circle of the base end of the projection 32. When the projection 32 has a square columnar shape, the width W is a diagonal length of the square base end of the projection 32.

For example, when the projection 32 of the microneedle 30 is formed in a pyramid shape having an acute angle on the distal end and is pierced into the target to pass through the stratum corneum, a point angle θ of the projection 32 is preferably in the range between 5 degrees or more and 30 degrees or less, more preferably, in the range between 10 degrees or more and 20 degrees or less.

When the microneedle 30 is pierced into the target and the projection 32 reaches inside the stratum corneum, the point angle θ of the projection 32 is preferably 30 degrees or more, more preferably 45 degrees or more. The point angle θ of the projection 32 is a maximum angle of the projection 32 in a cross section in a direction perpendicular to the projection forming surface 31a of the base 31.

The forming material of the microneedle 30 is a compatible material having a biocompatibility, and the compatible material has properties that exhibit functions for the intended purpose without affecting the body. Examples of the compatible material include water-soluble polymer, water-insoluble polymer, biopolymer, non-metal, metal and resin that do not affect the body.

When the compatible material is a water-soluble polymer, examples of the compatible material include alginates, curdlan, chitin, chitosan, glucomannan, polymalic acid, collagen, collagen peptide, hydroxypropyl cellulose and gelatin. When the compatible material is a non-metal, examples of the compatible material include silicon, and when the compatible material is a metal, examples of the compatible material include titanium. When the compatible material is a resin, examples of the compatible material include silicone and polyglycolic acid.

Of the compatible materials, chitin, chitosan and chitosan derivatives include those derived from crustacea such as crab and shrimp, generated by mycelium or microorganisms and having those as a starting material. Chitosan, a mixture of chitin and chitosan, and a mixture of chitin and chitosan derivative are preferable as a forming material of the microneedle 30 since they have an aesthetic effect, sterilization effect and antibacterial effect to the skin.

Although there is no clear distinction between chitin and chitosan, chitin with deacetylation of 70% or more is generally referred to as chitosan. Deacetylation of chitin may be performed by using a known technique.

The forming material of the base body 31 and the forming material of the projection 32 may be the same or different from each other. Considering that the base 31 and the projection 32 are integrally formed, the forming material of the base body 31 and the forming material of the projection 32 are preferably the same.

The microneedle 30 may have a delivery substance contained inside the microneedle 30 or applied on the outer surface of the microneedle 30. Examples of delivery substance contained microneedle 30 include physiologically active substances and cosmetic compositions. The delivery substance may be aromatic materials. When the delivery substance is an aromatic material, the microneedle 30 is preferably used as a cosmetic since the microneedle 30 can be used to apply fragrance to the target. The delivery substance may be biopharmaceuticals. Biopharmaceuticals are drugs which use materials derived from cells and cell tissues of human or animals.

The delivery substance may be applied on the skin in which a hole is formed after the microneedle 30 is pierced into the target. As a consequence, the delivery substance is delivered into the body of target via the hole formed by the microneedle 30. Here, the microneedle 30 may have a delivery substance contained inside the microneedle 30 or carried on the outer surface of the microneedle 30. Alternatively, the projections 32 of the microneedle 30 can be embedded in the skin of target.

As described above, according to the microneedle unit 10 and the microneedle container 20 of the first embodiment, the following effect can be achieved.

(1) When the microneedle container 20 is subject to vibration in the extending direction of the microneedle 30 and the microneedle 30 in the microneedle container 20 is displaced, the projection 32 of the microneedle 30 is prevented from colliding with the cover facing surface 44. In addition to that, the projection 32 of the microneedle 30 is less likely to be displaced into a gap between the abutment surface 42 and the supporting surface 53. As a consequence, when the microneedle container 20 is subject to vibration in the extending direction of the projection 32, the projection 32 of the microneedle 30 is prevented from being deformed.

(2) The adhesive strength of the abutment surface 42 and the adhesive strength of the supporting surface 53 may be different from each other. In this case, when the microneedle container 20 is opened, the microneedle 30 is easily held by the microneedle container 20 if the microneedle 30 is in contact with the surface having a high adhesive strength.

(3) The close-contact section 46 may be located on at least part of the abutment surface 42, and the close-contact section 46 may protrude in the extending direction from the contact surface 48 located outside the close-contact section 46. In this case, when the microneedle container 20 is opened, the microneedle 30 is easily held on the close-contact section 46, and the microneedle 30 on the close-contact section 46 protrudes in the extending direction from the contact surface 48. As a consequence, the microneedle 30 can be easily taken out from the cover 21 which is an example of the close contact member.

<Modification Examples of First Embodiment>

Figure 8A:
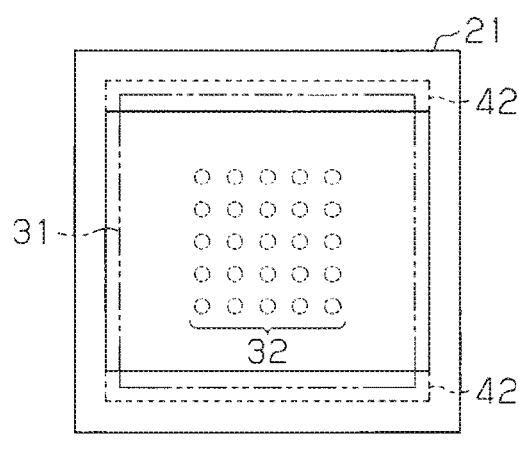
FIG. 8(a) is a plan view which shows a plan configuration of the cover as seen from the wall surface having the cover facing surface according to a modification example.
Figure 8B:
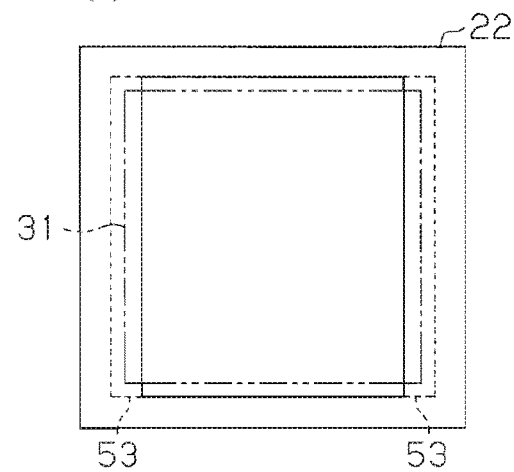
FIG. 8(b) is a plan view which shows a plan configuration of the housing as seen from the wall surface having the housing facing surface according to the modification example.
Figure 9A:
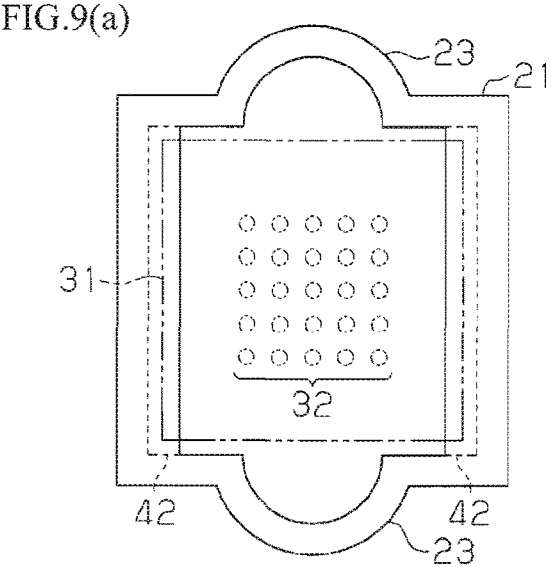
FIG. 9(a) is a plan view which shows a plan configuration of the cover as seen from the wall surface having the cover facing surface according to the modification example.
Figure 9B:
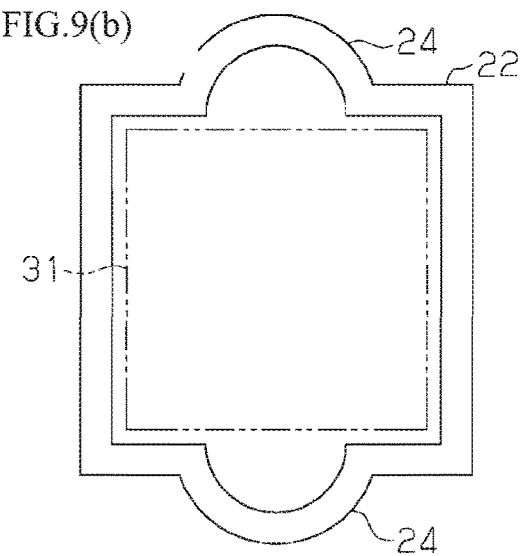
FIG. 9(b) is a plan view which shows a plan configuration of the housing as seen from the wall surface having the housing facing surface according to the modification example.
Figure 11:
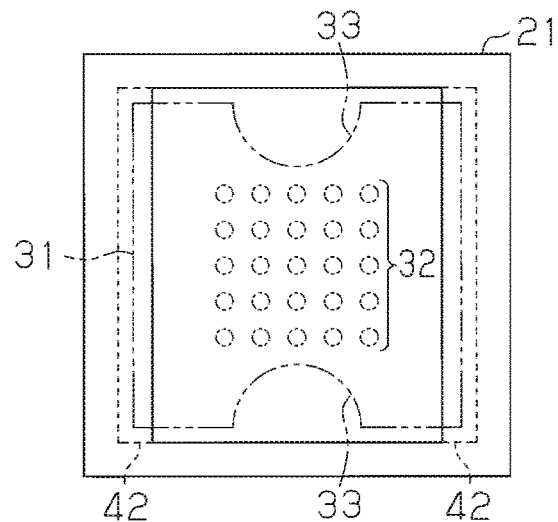
FIG. 11 is a plan view which shows a plan configuration of the cover as seen from the wall surface having a cover facing surface according to the modification example.

The above first embodiment may be appropriately modified as below. FIGS. 8(a), 9(a) and 11 are plan views similar to FIG. 3, which show a plan configuration of the cover 21 as seen from the wall surface having the cover facing surface 44. Further, FIGS. 8(b) and 9(b) are plan views which show a plan configuration of the housing 22 as seen from the wall surface having the housing facing surface 55. In FIGS. 8(a), 9(a) and 11, for the convenience of explanation of the arrangement of the abutment surface 42 of the cover 21, the wall surface having the cover facing surface 44 is not illustrated and the abutment surface 42 formed on the cover 21 is illustrated by the dotted line. In FIGS. 8(b) and 9(b), for the convenience of explanation of the arrangement of the supporting surface 53 of the housing 22, the wall surface having the housing facing surface 55 is not illustrated and the supporting surface 53 formed on the housing 22 is illustrated by the dotted line.

With reference to FIG. 8, the positions of the abutment surface 42 of the cover 21 and the supporting surface 53 of the housing 22 as seen in the stacking direction of the housing 22 and the cover 21 will be described.

As shown in FIG. 8(a), the abutment surfaces 42 are provided to overhang from each of two opposing surfaces on the inner surface of the cover 21. Each of two abutment surfaces 42 are entirely located on each surface in a direction perpendicular to a direction in which the aforementioned two opposing surfaces oppose to each other.

On the other hand, as shown in FIG. 8(b), the supporting surfaces 53 are provided to overhang from each of two opposing surfaces on the inner surface of the housing 22. Further, a direction in which each of the overhanging surfaces of the supporting surfaces 53 oppose to each other is a direction perpendicular to a direction in which each of the extending surfaces of the abutment surfaces 42 oppose to each other when the microneedle container 20 is assembled.

Accordingly, when the microneedle container 20 is assembled, part of the abutment surface 42 and part of the supporting surface 53 overlap each other in the stacking direction of the cover 21 and the housing 22. Furthermore, part of the supporting surface 53 and part of the abutment surfaces 42 overlap each other in the stacking direction of the cover 21 and the housing 22. In other words, the abutment surface 42 that supports the microneedle 30 and the supporting surface 53 may not necessarily be arranged in plane symmetry with respect to the surface on which the microneedle 30 is located.

As shown in FIG. 9(a), the cover 21 shown in FIG. 1 may include a cover bulging portion 23 that protrudes outward from the outer periphery of the cover 21. The cover 21 includes, for example, two cover bulging portions 23, and the two cover bulging portions 23 are arranged in plan view so as not to overlap the two abutment surfaces 42 and oppose to each other in the direction perpendicular to the opposing direction described above.

As shown in FIG. 9(b), the housing 22 may be formed of a bottom and a side wall which does not have a stepped surface. Furthermore, the housing 22 may include a housing bulging portion 24 that protrudes outward from the outer periphery of the housing 22. The housing 22 includes, for example, two housing bulging portions 24, and the two housing bulging portions 24 oppose to each other in the direction perpendicular to the opposing direction described above in plan view. Accordingly, when the microneedle container 20 is assembled, the positions of the cover bulging portions 23 each overlap the housing bulging portions 24 in the stacking direction of the cover 21 and the housing 22.

In this configuration, when the microneedle 30 is disposed in the cover 21 in the state that the microneedle container 20 is open, a user of the microneedle 30 can put his/her finger in an area within the cover bulging portions 23. This helps the user hold the microneedle 30 with his/her two fingers. As a result, the microneedle 30 can be easily taken out from the cover 21.

In addition, when the microneedle 30 is disposed in the housing 22 in the state that the microneedle container 20 is open, a user of the microneedle 30 can also put his/her finger in an area within the housing bulging portion 24. This helps the user hold the microneedle 30 in the same manner as that when the microneedle 30 is disposed in the cover 21. As a result, the microneedle 30 can be easily taken out from the housing 22.

The cover 21 may include one cover bulging portion 23, or may include three or more cover bulging portions 23. Further, the housing 22 may include one housing bulging portion 24 or may include three or more housing bulging portions 24.

Figure 10:
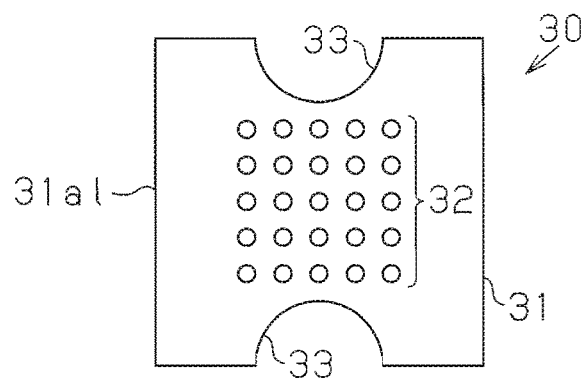
FIG. 10 is a top view which shows a top view of a projection forming surface of the microneedle according to the modification example.

As shown in FIG. 10, the microneedle 30 may include a notch 33 in the abutted section 31a1 of the base 31. The notch 33 is notched inward from the outer edge of the abutted section 31a1. For example, the microneedle 30 includes two notches 33. The notch 33 is each located at the center of each side that forms the outer edge of the base 31 having a rectangular plate shape so that two notches 33 oppose to each other with a plurality of projections 32 interposed therebetween.

As shown in FIG. 11, when the microneedle 30 is housed in the microneedle container 20 shown in FIG. 1, the notches 33 of the microneedle 30 are located between two abutment surfaces 42 in the opposing direction described above. As a consequence, when the microneedle 30 is disposed in the cover 21 in the state that the microneedle container 20 is open, a user of the microneedle 30 can hold the microneedle 30 with his/her fingers put in the notches 33. As a result, the microneedle 30 can be easily taken out from the cover 21.

In addition, when the microneedle 30 is disposed in the housing 22 in the state that the microneedle container 20 is open, a user of the microneedle 30 can also hold the microneedle 30 in the same manner as that when the microneedle 30 is disposed in the cover 21. As a result, the microneedle 30 can be easily taken out from the housing 22.

The microneedle 30 may include one notch 33, or may include three or more notches 33. Further, the notch 33 may be located not only at the center of each side that forms the outer edge of the base 31, but also on an end of each side or at the corner formed by two sides of the base 31. When the microneedle 30 include two or more notches 33, two notches 33 may not necessarily be located at positions opposed to each other with a plurality of projections 32 therebetween.

Further, when the microneedle 30 is housed in the microneedle container 20, the notch 33 may be located at a position that overlaps one abutment surface 42 in the opposing direction. In this configuration, the microneedle 30 still can be easily taken out from the cover 21 since the microneedle 30 has the notch 33.

<Second Embodiment>

With reference to FIGS. 12 to 23, a second embodiment of a microneedle unit and a microneedle container according to the technique of the present disclosure will be described. The microneedle unit and the microneedle container of the second embodiment have a configuration different from that of the microneedle unit and the microneedle container of the first embodiment in the configuration of the abutment section and the supporting section of the microneedle container. Those differences will be described in detail in the following description. While the detailed description of the other configurations is omitted, a plurality of exemplary configurations of the microneedle unit, and examples will be each described below. Furthermore, in FIGS. 12 to 23, the same elements as those described in the first embodiment are denoted by the same reference numerals.

<Configuration of Microneedle Unit>

Figure 12:
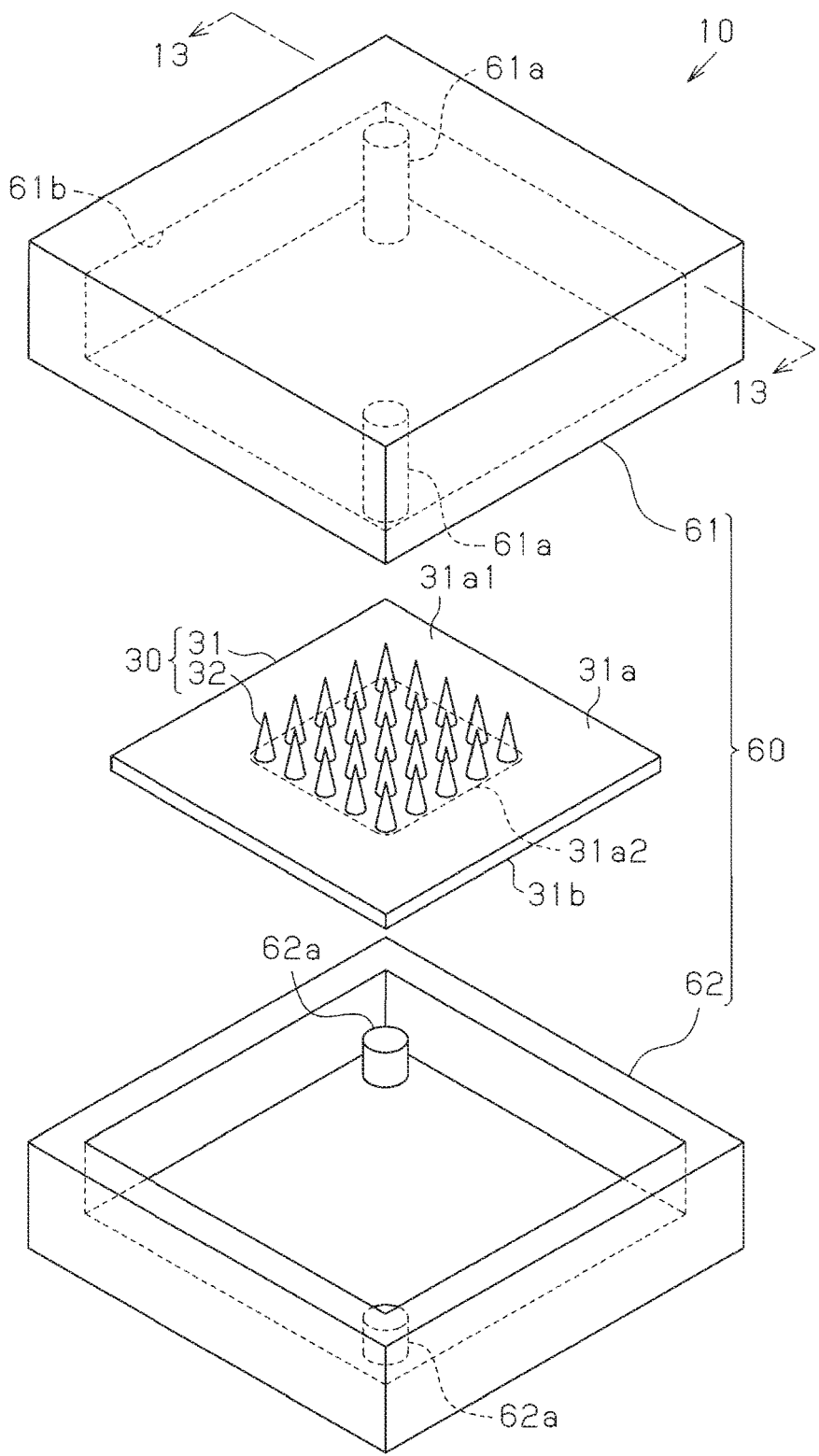
FIG. 12 is an exploded perspective view which shows an exploded perspective configuration of a microneedle unit according to a second embodiment of the present disclosure.
Figure 13:
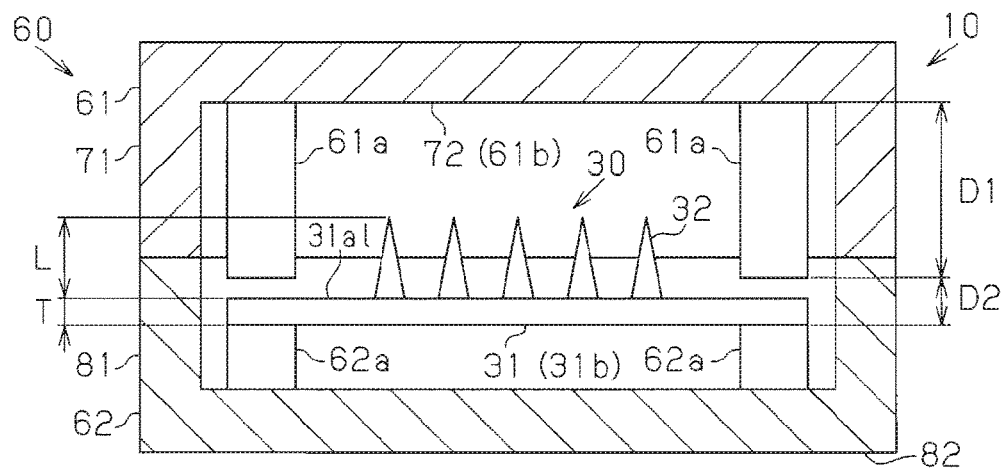
FIG. 13 is a cross sectional view, taken along the line 13-13 of FIG. 12, which shows a cross sectional configuration of the microneedle unit.
Figure 14:
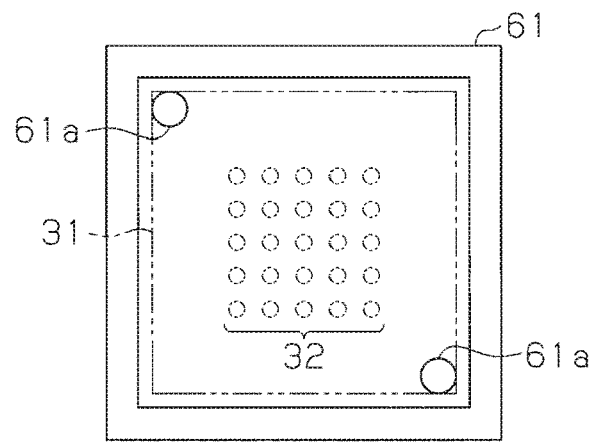
FIG. 14 is a plan view which shows a plan configuration of the cover as seen from a cover bottom in the microneedle unit according to the second embodiment.
Figure 15:
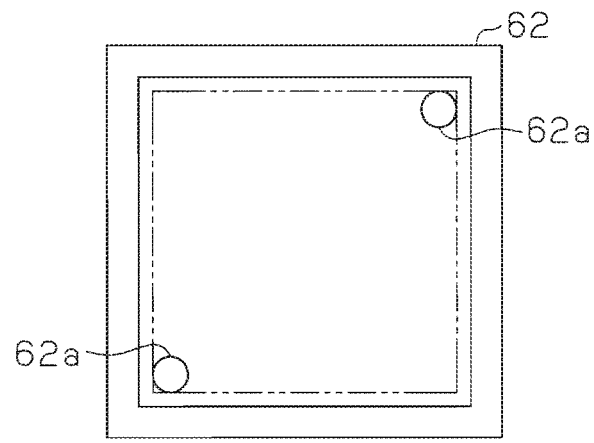
FIG. 15 is a plan view which shows a plan configuration of the housing as seen from a housing bottom in the microneedle unit according to the second embodiment.

With reference to FIGS. 12 to 23, a configuration of a microneedle unit will be described. FIG. 14 is a plan view which shows a plan configuration of a cover as seen from a cover bottom of the cover 21 of the microneedle container 20, and FIG. 15 is a plan view which shows a plan configuration of a housing as seen from a housing bottom of the housing of the microneedle container. In FIG. 14, for the convenience of explanation of the arrangement of the cover protruding members of the cover, the cover bottom is not illustrated. In FIG. 15, for the convenience of explanation of the arrangement of the housing protruding members of the housing, the housing bottom is not illustrated.

As shown in FIG. 12, the microneedle unit 10 includes a microneedle container 60 and the microneedle 30.

The microneedle container 60 includes a cover 61 and a housing 62. The cover 61 includes a cover protruding member 61a and a facing section 61b that faces the projections 32. At the distal end of the cover protruding member 61a, an abutment section that faces the abutted section 31a1 of the base 31 is provided. The housing 62 includes a housing protruding member 62a, and a supporting section that supports the supported surface 31b of the base 31 is provided on the distal end of the housing protruding member 62a.

In the cover 61, the distance between the distal end of the cover protruding member 61a and the facing section 61b is larger than the length of the projection 32 in the extending direction. Furthermore, the distance between the distal end of the cover protruding member 61a and the distal end of the housing protruding member 62a is smaller than the sum of a thickness of the base 31 in the extending direction and the length of the projection 32.

That is, in the microneedle container 60, the distance between the distal end of the cover protruding member 61a and the facing section 21b in the extending direction is larger than the distance between the abutted section 31a1 and the distal end of the projection 32. Furthermore, the distance between the distal end of the cover protruding member 61a and the distal end of the housing protruding member 62a is smaller than the sum of the distance between the abutted section 31a1 and the supported surface 31b and the distance between the abutted section 31a1 and the distal end of the projection 32.

As shown in FIG. 13, the cover 61 of the microneedle container 60 is a recess-shaped member, and the cover 61 is formed, for example, in a rectangular tubular shape with one of two tubular ends closed. Alternatively, the cover 61 may be formed in a hemisphere, elliptical hemisphere shape, or a circular tubular shape.

The cover 61 includes a cover tubular body 71 having two cover tubular ends, and a cover bottom 72 formed in a plate shape that closes one of the cover tubular ends of the cover tubular body 71, and the cover bottom 72 includes a facing section 61b that faces the projections 32 of the microneedle 30. Although the cover bottom 72 has a plate shape, the cover bottom 72 may have a curved plate shape.

The cover 61 includes two cover protruding members 61a, and the cover protruding members 61a extend from the cover bottom 72 toward the cover tubular end of the cover tubular body 71, which is open. The cover protruding member 61a has one end in contact with the cover bottom 72, which is a proximal end, and the other end located spaced from the cover bottom 72, which is a distal end. The distal end of the cover protruding member 61a is an abutment section that abuts the abutted section 31a1 of the base 31.

Each cover protruding member 61a has, for example, a circular columnar shape. Further, the cover protruding member 61a is not limited to a circular columnar shape, and may be a pyramid shape or a frustum shape. When the cover protruding member 61a has a pyramid shape, the pyramid shape may be a polygonal pyramid shape or a cone shape. When the cover protruding member 61a has a pyramid shape, the bottom of the pyramid shape is preferably in contact with the cover bottom 72. When the cover protruding member 61a has a frustum shape, the frustum shape may be a truncated polygonal shape or a truncated cone shape. Each cover protruding member 61a may have a polygonal columnar shape. Two cover protruding members 61a may have the shapes that are the same or different from each other.

The distance between the distal end of the cover protruding member 61a and the cover bottom 72 is the facing distance D1, and the facing distance D1 is larger than the length L of the projection 32 in the extending direction. As a consequence, when the microneedle container 60 is subject to vibration in the extending direction of the microneedle 30 and the microneedle 30 in the microneedle container 60 is displaced, the projection 32 of the microneedle 30 is prevented from colliding with the cover bottom 72.

As shown in FIG. 14, one of two cover protruding members 61a is located at a corner on the inner surface of the cover bottom 72, and the other of two cover protruding members 61a is located at a corner on the diagonal line which passes through the corner on which one of the cover protruding members 61a is located. Further, each of the cover protruding members 61a may be located at any positions on the cover bottom 72 as long as they face the abutted section 31a1 of the base 31.

As shown in FIG. 13, the housing 62 is a recess-shaped member, and the housing 62 is formed, for example, in a rectangular tubular shape with one of two tubular ends closed. Alternatively, the housing 62 may be formed in a hemisphere, elliptical hemisphere shape, or a circular tubular shape.

The housing 62 includes a housing tubular body 81 having two housing tubular ends, and a housing bottom 82 formed in a plate shape that closes one of the housing tubular ends. Although the housing bottom 82 has a plate shape, the housing bottom 82 may have a curved plate shape.

The housing 62 includes two housing protruding members 62a, and the housing protruding members 62a extend from the housing bottom 82 toward the housing tubular end of the housing tubular body 81, which is open. The housing protruding member 62a has one end in contact with the housing bottom 82, which is a proximal end, and the other end located spaced from the housing bottom 82, which is a distal end. The distal end of the housing protruding member 62a is a supporting section that supports the supported surface 31b of the base 31.

Each housing protruding member 62a has, for example, a circular columnar shape. Further, the housing protruding member 62a is not limited to a circular columnar shape, and may be a pyramid shape or a frustum shape. When the housing protruding member 62a has a pyramid shape, the pyramid shape may be a polygonal pyramid shape or a cone shape. When the housing protruding member 62a has a pyramid shape, the bottom of the pyramid shape is preferably in contact with the housing bottom 82. When the housing protruding member 62a has a frustum shape, the frustum shape may be a truncated polygonal shape or a truncated cone shape. Each housing protruding member 62a may have a polygonal columnar shape. Two housing protruding members 62a may have the shapes that are the same or different from each other.

Furthermore, a distance between the distal end of the cover protruding member 61a and the distal end of the housing protruding member 62a is the nipping distance D2, and the nipping distance D2 is smaller than the sum of the length L of the projection 32 and the thickness T of the base 31. As a consequence, the projection 32 does not come into contact with the inner surface of the microneedle container 60 when the base 31 is displaced in the thickness direction. Accordingly, the projection 32 of the microneedle 30 is prevented from being deformed when the microneedle container 60 is subject to vibration in the thickness direction of the base 31.

As shown in FIG. 15, one of two housing protruding members 62a is located at a corner on the inner surface of the housing bottom 82, and the other of two housing protruding members 62a is located at a corner on the diagonal line which passes through the corner on which one of the housing protruding members 62a is located.

In the housing 62, the position of the housing protruding member 62a and the position of the cover protruding member 61a overlap each other as seen in the stacking direction of the housing 62 and the cover 61 when the microneedle container 60 is assembled. As a consequence, the position of the microneedle 30 can be more reliably stabilized compared with the configuration in which the position of the housing protruding member 62a and the position of the cover protruding member 61a do not overlap each other as seen in the stacking direction of the housing 62 and the cover 61.

Further, each of the housing protruding member 62a may be located at any positions on the housing bottom 82 as long as they face the supported surface 31b of the base 31.

Figure 16:
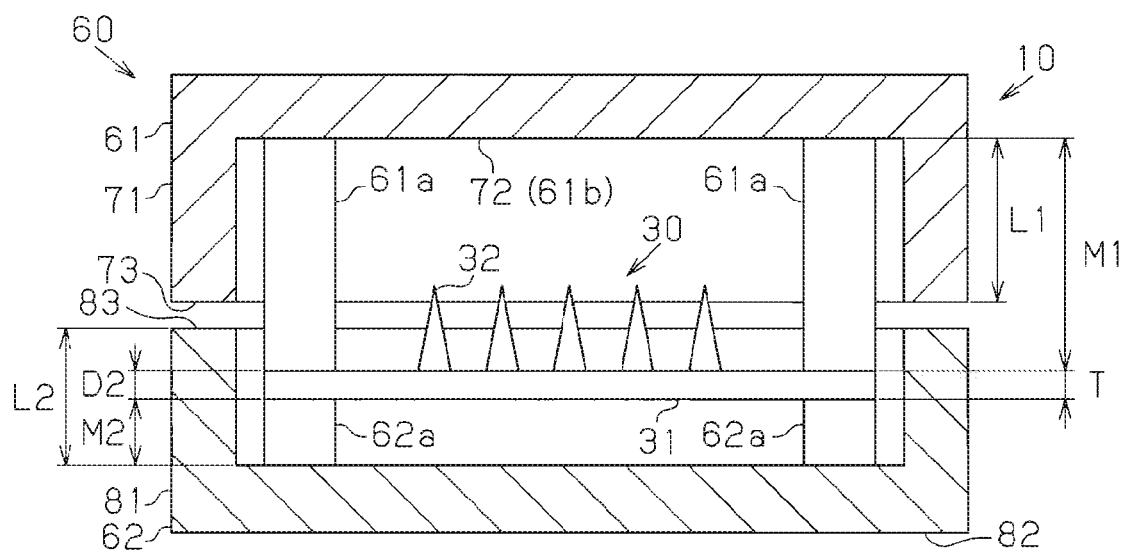
FIG. 16 is a cross sectional view which shows a cross sectional configuration of the microneedle unit according to the second embodiment.

As shown in FIG. 16, the distal end of the cover protruding member 61a and the distal end of the housing protruding member 62a may be configured to be simultaneously in contact with the base 31 when the microneedle 30 is housed in the microneedle container 60.

The length from the inner surface of the cover bottom 72 to the cover tubular end 73 which is open to the housing 62 is a cover length L1, and the length from the inner surface of the cover bottom 72, that is, the proximal end of the cover protruding member 61a to the distal end of the cover protruding member 61a is a cover protruding member length M1. Furthermore, the length from the inner surface of the housing bottom 82 to the housing tubular end 83 which is open to the cover 61 is a housing length L2, and the length from the inner surface of the housing bottom 82, that is, the proximal end of the housing protruding member 62a to the distal end of the housing protruding member 62a is a housing protruding member length M2.

When the cover length L1, the cover protruding member length M1, the housing length L2 and the housing protruding member length M2 satisfy the following formula 1, the distal end of the cover protruding member 61a and the distal end of the housing protruding member 62a are simultaneously in contact with the base 31.

$$(L1+L2)<(M1+M2)$$ (Formula 1)

The cover length L1 may be equal to the cover protruding member length M1, or may be larger or smaller than the cover protruding member length M1 as long as the above relation is satisfied. Alternatively, the cover length L1 may be equal to the housing length L2, or may be larger or smaller than the housing length L2. Further, the housing length L2 may be equal to the housing protruding member length M2, or may be larger or smaller than the housing protruding member length M2. Alternatively, the housing protruding member length M2 may be equal to the cover protruding member length M1, or may be larger or smaller than the cover protruding member length M1.

In the configuration that satisfies the above formula 1, the rigidity of the cover protruding member 61a may be substantially equal to the rigidity of the other portion of the cover 61 than the cover protruding member 61a, and the rigidity of the housing protruding member 62a may be substantially equal to the rigidity of the other portion of the housing 62 than the housing protruding member 62a. In this configuration, a gap is formed between the cover tubular end 73 of the cover 61 and the housing tubular end 83 of the housing 62 in the state that the microneedle 30 is housed in the microneedle container 60. Since the nipping distance D2 is equal to the thickness T of the base 31, the microneedle 30 is supported in a stable manner compared with the configuration in which the nipping distance D2 is larger than the thickness T.

More preferably, the cover length L1, cover protruding member length M1, housing length L2 and housing protruding member length M2 along with the thickness T of the base 31 of the microneedle 30 satisfy the following formula 2.

$$(L1+L2) \leq (M1+M2+T)$$ (Formula 2)

In the formula 2, the right side of the formula 1 includes the thickness T. Accordingly, the formula 2 is satisfied if the difference between the sum of the cover length L1 and the housing length L2 and the sum of the cover protruding member length M1 and the housing protruding member length M2 is smaller than that of the formula 1. As a consequence, a gap is less likely to be formed between the cover tubular end 73 of the cover 61 and the housing tubular end 83 of the housing 62. Since the microneedle 30 housed in the microneedle container 60 is less likely to be exposed to the outside, a configuration that satisfies the formula 2 is more preferable.

Figure 17:
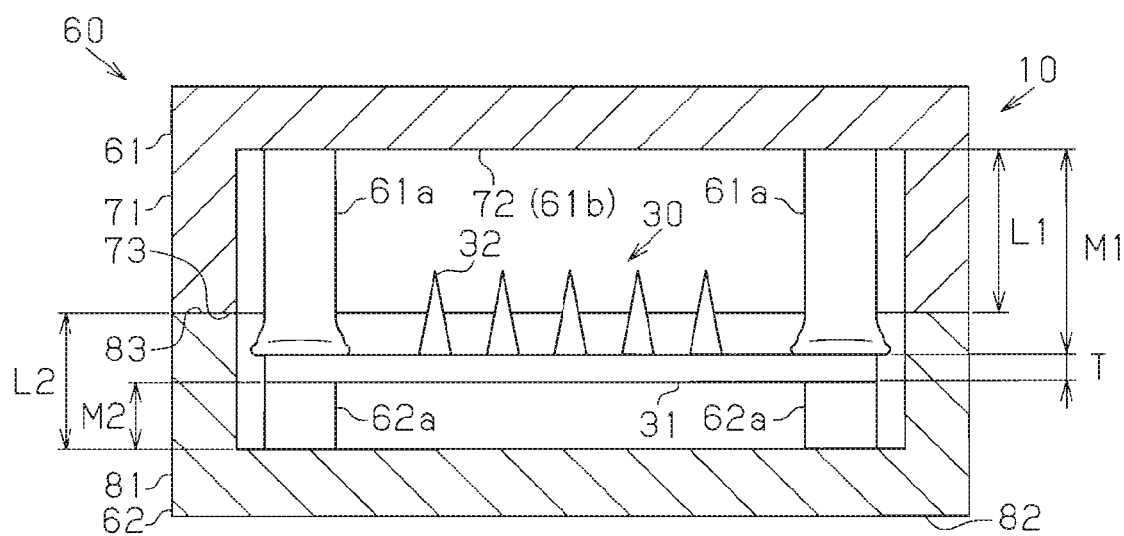
FIG. 17 is a cross sectional view which shows a cross sectional configuration of the microneedle unit according to the second embodiment.

As shown in FIG. 17, when the above formula 1 or the formula 2 is satisfied, at least one of the cover protruding member 61a and the housing protruding member 62a is preferably made of an elastic material. When the forming material of the cover protruding member 61a is an elastic material, the cover protruding member 61a preferably has elasticity higher than the elasticity of the other portion of the cover 61 than the cover protruding member 61a. Further, when the forming material of the housing protruding member 62a is an elastic material, the housing protruding member 62a preferably has elasticity higher than the elasticity of the other portion of the housing 62 than the housing protruding member 62a.

When the forming material of the cover protruding member 61a is an elastic material, the cover protruding member 61a is an example of the elastic section, and the cover 61 is an example of the elastic member. When the forming material of the housing protruding member 62a is an elastic material, the housing protruding member 62a is an example of the elastic section, and the housing 62 is an example of the elastic member.

When the forming material of the cover protruding member 61a is an elastic material, the forming material of the cover 61 is a material selected from a group of the aforementioned forming materials of the cover 21.

The forming material of the cover protruding member 61a is, for example, silicone resin, urethane resin and porous material, and, when the forming material is a porous material, the porous material is sponge or the like. When the forming material of the cover protruding member 61a is a silicone resin, the forming material of the cover 61 may be any of the aforementioned materials other than a silicone resin, and any of the forming materials having elasticity lower than that of the silicone resin. When the forming material of the cover protruding member 61a is a urethane resin and a porous material, the forming material of the cover 61 may be any of the aforementioned materials having elasticity lower than that of the urethane resin and the porous material.

When the forming material of the cover protruding member 61a is an elastic material and the above formula 1 is satisfied, the cover protruding member 61a is pressed against the base 31 in the state in which the cover tubular end 73 and the housing tubular end 83 are in contact with each other, and this causes the distal end of the cover protruding member 61*a* to be deformed. That is, the length of the cover protruding member 61*a* in the extending direction varies depending on whether the cover tubular end 73 and the housing tubular end 83 are in contact with each other or not. In addition, when the right side of the above formula 2 becomes larger than the left side, the distal end of the cover protruding member 61*a* is also deformed. This also allows the cover protruding member 61*a* to be in more close contact with the base 31, and accordingly, the microneedle 30 is held by the microneedle container 60 in a more stable manner. The cover tubular end 73 and the housing tubular end 83 are an example of the contact section.

Moreover, since the distal end of the cover protruding member 61*a* is deformed when the microneedle 30 is housed in the microneedle container 60, a gap is prevented from being formed between the opened cover tubular end 73 of the cover 61 and the opened housing tubular end 83 of the housing 62. As a result, the microneedle 30 is less likely to be exposed to the outside of the housing space of the microneedle container 60.

More preferably, the cover length L1, cover protruding member length M1, housing length L2 and housing protruding member length M2 along with the thickness T of the base 31 of the microneedle 30 satisfy the following formula 3.

$$(L1+L2)<(M1+M2+T) \tag{Formula 3}$$

Similarly to the formula 2, the formula 3 is satisfied if the difference between the sum of the cover length L1 and the housing length L2 and the sum of the cover protruding member length M1 and the housing protruding member length M2 is smaller than that of the formula 1. As a consequence, the cover protruding member 61*a* is more closely in contact with the base 31, and a gap is further less likely to be formed between the cover tubular end 73 of the cover 61 and the housing tubular end 83 of the housing 62.

In addition, when the cover 61 includes a plurality of cover protruding members 61*a*, the forming material of all the cover protruding members 61*a* may be the aforementioned elastic material, or the forming material of part of the plurality of cover protruding members 61*a* may be the aforementioned elastic material.

Moreover, similarly to the case where the forming material of the cover protruding member 61*a* is an elastic material, when the forming material of the housing protruding member 62*a* is an elastic material, the forming material of the housing protruding member 62*a* may be any of the aforementioned forming materials and the forming material of the housing 62 may be any of the aforementioned forming materials. In addition, when the housing 62 includes a plurality of housing protruding members 62*a*, the forming material of all the housing protruding members 62*a* may be the aforementioned forming material having elasticity, or the forming material of part of the plurality of housing protruding members 62*a* may be the aforementioned forming material having elasticity. Alternatively, both the forming material of the cover protruding member 61*a* and the forming material of the housing protruding member 62*a* may be an elastic material.

Figure 18:
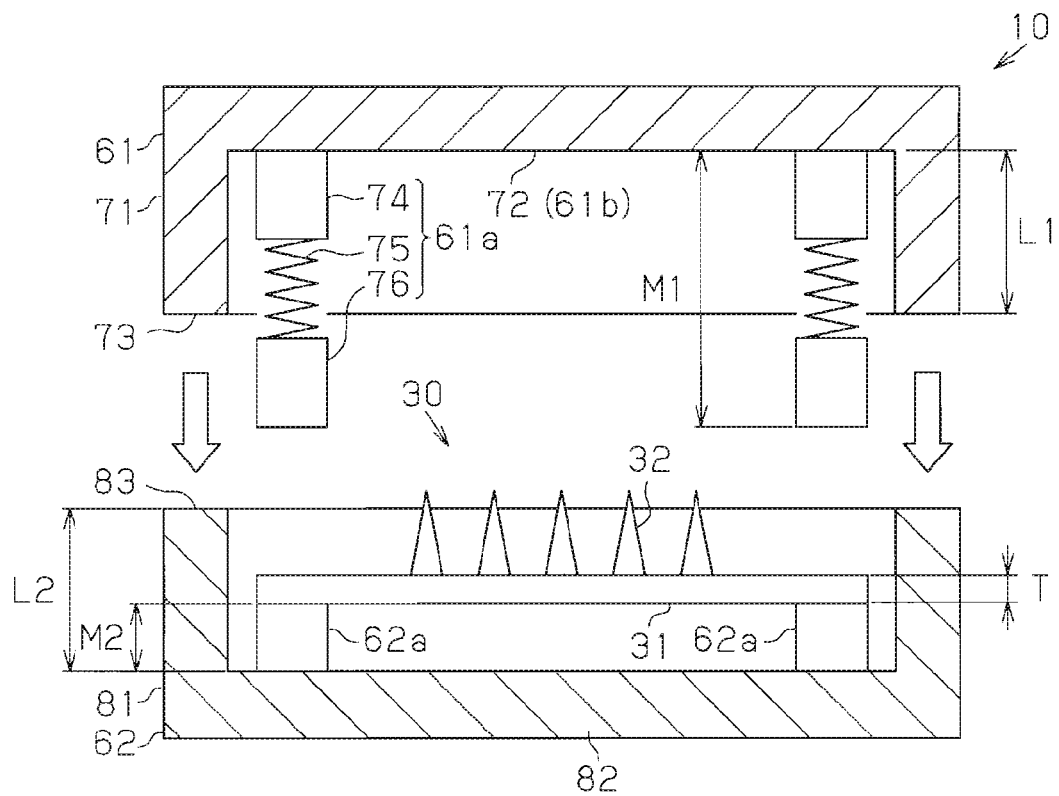
FIG. 18 is an exploded cross sectional view which shows an exploded cross sectional configuration of the microneedle unit according to the second embodiment.

As shown in FIG. 18, when the above formula 1 is satisfied, at least one of the cover protruding member 61*a* and the housing protruding member 62*a* is preferably an elastic section having an elastic mechanism. Preferably, the elasticity of the cover protruding member 61*a* is higher than the elasticity of the other portion of the cover 61 than the cover protruding member 61*a*. Further, when the housing protruding member 62*a* is an elastic section, the housing protruding member 62*a* preferably has the elasticity higher than the elasticity of the other portion of the housing 62 than the housing protruding member 62*a*. When the cover protruding member 61*a* is an elastic section, the cover 61 is an example of the elastic member, and when the housing protruding member 62*a* is an elastic section, the housing 62 is an example of the elastic member.

The forming material of the cover 61 may be any of the above forming materials. The cover protruding member 61*a* includes, for example, a bottom contact section 74 which is a non-elastic material and is in contact with the cover bottom 72, an elastic mechanism 75 and a base contact section 76 which is a non-elastic material and is in contact with the base 31. For example, the forming material of the bottom contact section 74 and the base contact section 76 may be the same as the aforementioned forming material of the cover 61. The elastic mechanism 75 is, for example, a spring mechanism, a piston mechanism or the like. Further, the cover protruding member 61*a* may not necessarily include a portion not having elasticity, that is, the entire portion of the cover protruding member 61*a* may be formed of an elastic mechanism.

Figure 19:
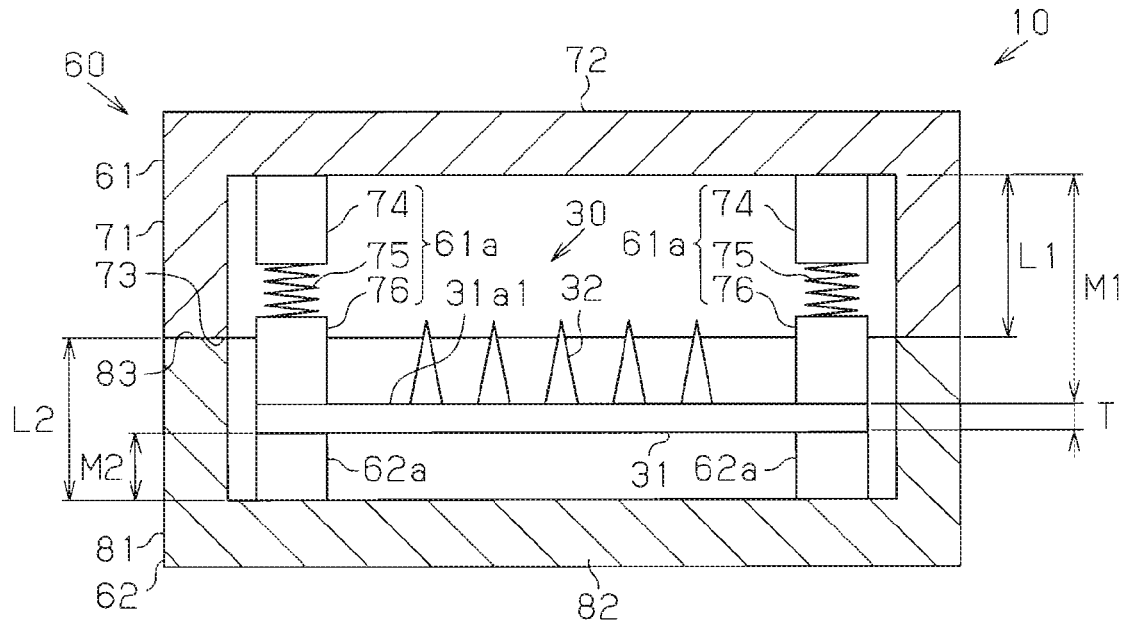
FIG. 19 is a cross sectional view which shows a cross sectional configuration of the microneedle unit according to the second embodiment.

As shown in FIG. 19, when the cover 61 is in contact with the housing 62 and thus the cover tubular end 73 is in contact with the housing tubular end 83, the cover protruding member 61*a* is pressed against the abutted section 31*a*1 of the base 31, and this causes the elastic mechanism 75 of the cover protruding member 61*a* to be deformed. Accordingly, the length of the cover protruding member 61*a* in the extending direction decreases from the length in the state in which the cover tubular end 73 and the housing tubular end 83 are not in contact with each other, and this causes the cover protruding member 61*a* to be in more close contact with the base 31. As a result, the microneedle 30 is supported by the microneedle container 60 in a more stable manner.

Moreover, since a gap is prevented from being formed between the opened cover tubular end 73 of the cover 61 and the opened housing tubular end 83 of the housing 62, the microneedle 30 is less likely to be exposed to the outside of the housing space of the microneedle container 60.

Figure 20:
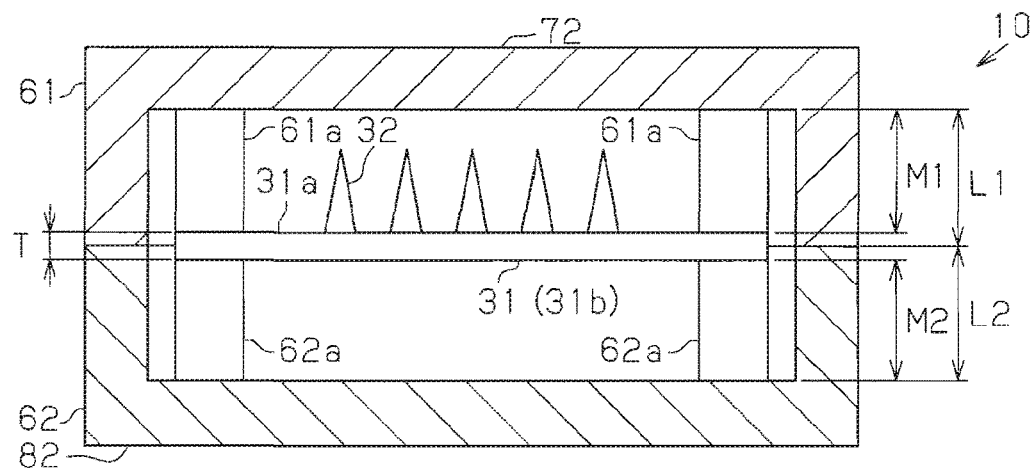
FIG. 20 is a cross sectional view which shows a cross sectional configuration of the microneedle unit according to the second embodiment.

As shown in FIG. 20, when the formula 4 is satisfied, it is preferable that the cover length L1 is equal to the housing length L2, and the cover protruding member length M1 is equal to the housing protruding member length M2.

$$(L1+L2)=(M1+M2+T) \tag{Formula 4}$$

When the microneedle 30 is housed in the microneedle container 60, the projection 32 of the microneedle 30 faces the housing bottom 82 but is not in contact with the housing 62. Accordingly, when the microneedle 30 is housed in the microneedle container 60, a surface of the base 31 which faces the cover bottom 72 may be the projection forming surface 31*a* or the supported surface 31*b*. As a result, the microneedle 30 can be easily housed in the microneedle container 60.

When the cover length L1 is equal to the housing length L2 and the cover protruding member length M1 is equal to the housing protruding member length M2, the position of the cover protruding member 61*a* in the cover 61 is preferably equal to the position of the housing protruding member 62*a* in the housing 62. That is, the cover 61 is preferably in the same shape as the housing 62. This allows for easy manufacturing and handling of the microneedle container 60 compared with the configuration in which the cover and the housing have the different shapes from each other. Specifically, since the cover 61 and the housing 62 are not need to be identified in the manufacturing process of the microneedle container 60, it is advantageous with regard to the manufacturing process compared with the configuration in which the cover 61 and the housing 62 are need to be identified. In addition, it is also advantageous with regard to stock control of the members used for the microneedle container 60 since there is no risk of shortage of either of the cover 61 and the housing 62.

Figure 21:
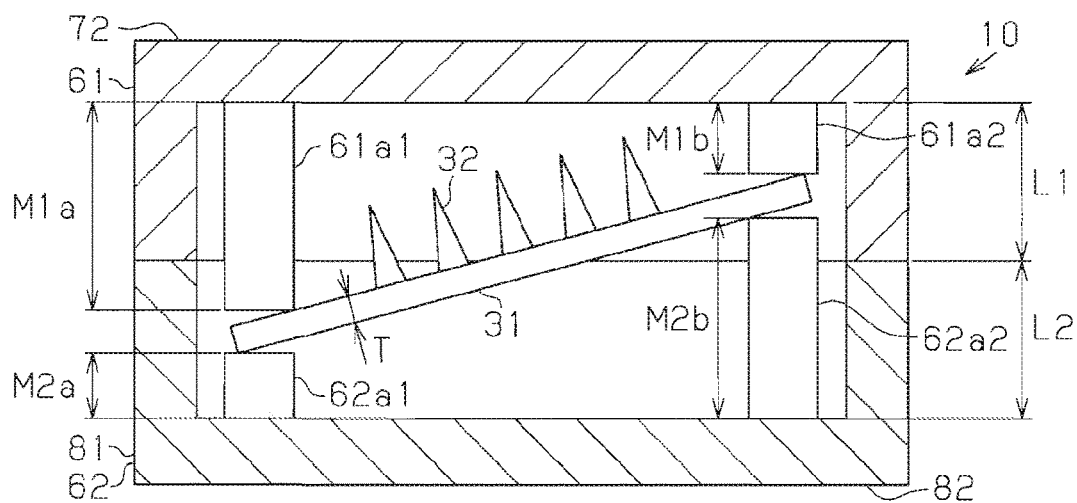
FIG. 21 is a cross sectional view which shows a cross sectional configuration of the microneedle unit according to the second embodiment.

As shown in FIG. 21, when the above formula 4 is substantially satisfied, two cover protruding members 61a may have the length different from each other and two housing protruding members 62a may have the length different from each other. The length of the first cover protruding member 61a1 is a first cover protruding member length M1a, and the length of the second cover protruding member 61a2 is a second cover protruding member length M1b. The first cover protruding member length M1a is larger than the second cover protruding member length M1b. Further, the length of the first housing protruding member 62a is a first housing protruding member length M2a, and the length of the second housing protruding member 62a2 is a second housing protruding member length M2b. The first housing protruding member length M2a is smaller than the second housing protruding member length M2b.

When the microneedle container 60 is assembled, the position of the first cover protruding member 61a1 and the position of the first housing protruding member 62a1 overlap each other and the position of the second cover protruding member 61a2 and the position of the second housing protruding member 62a2 overlap each other as seen in the stacking direction of the housing 62 and the cover 61. The first cover protruding member length M1a, the second cover protruding member length M1b, the first housing protruding member length M2a, the second housing protruding member length M2b and the thickness T of the base 31 substantially satisfy the following formula 5.

$$(M1a+M2a+T)=(M1b+M2b+T) \quad \text{(Formula 5)}$$

When the microneedle 30 is housed in the microneedle container 60, the base 31 of the microneedle 30 forms a predetermined angle to the housing bottom 82. As a consequence, when the microneedle 30 is housed in the microneedle container 60, the microneedle 30 is easily taken out compared with the configuration in which the base 31 of the microneedle 30 and the housing bottom 82 are parallel to each other.

Figure 22:
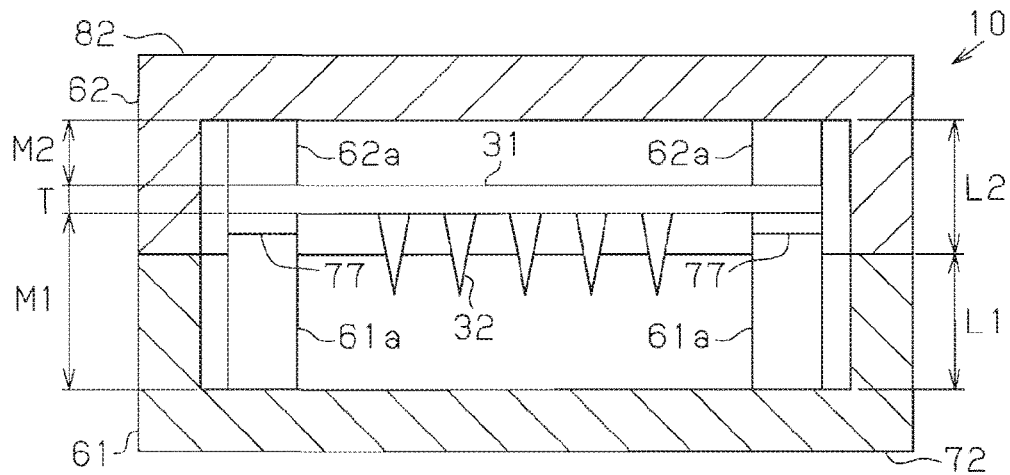
FIG. 22 is a cross sectional view which shows a cross sectional configuration of the microneedle unit according to the second embodiment.

As shown in FIG. 22, at least one of the distal end of the cover protruding member 61a and the distal end of the housing protruding member 62a may be provided with the close-contact section having an adhesive strength to the base 31 higher than that of the other portion. When the close-contact section is disposed on the distal end of the cover protruding member 61a, the close-contact section may have the adhesive strength to the base 31 higher than that of the other portion of the cover 61. When the close-contact section is disposed on the distal end of the housing protruding member 62a, close-contact section the close-contact section may have the adhesive strength to the base 31 higher than that of the other portion of the housing 62.

When the cover protruding member 61a includes the close-contact section 77, the close-contact section 77 may have a configuration less slippery to the base 31 compared with the other portion of the cover 61, or may be made of a forming material less slippery to the base 31 or more adhesive to the base 31. The configuration and the forming material of the close-contact section 77 may be any of the aforementioned close-contact sections 46.

Further, when only the cover protruding member 61a includes the close-contact section 77, the adhesive strength of the close-contact section 77 to the base 31 is preferably higher than the adhesive strength of the housing protruding member 62a to the base 31. When the adhesive strength of the close-contact section 77 is higher than the adhesive strength of the housing protruding member 62a, the cover protruding member length M1 is preferably larger than the cover length L1. This allows the microneedle 30 to be easily located on the close-contact section 77 when the microneedle 30 is taken out, and the microneedle 30 on the close-contact section 77 protrudes from the cover tubular body 71. As a consequence, the microneedle 30 can be easily taken out from the cover 21.

Figure 23:
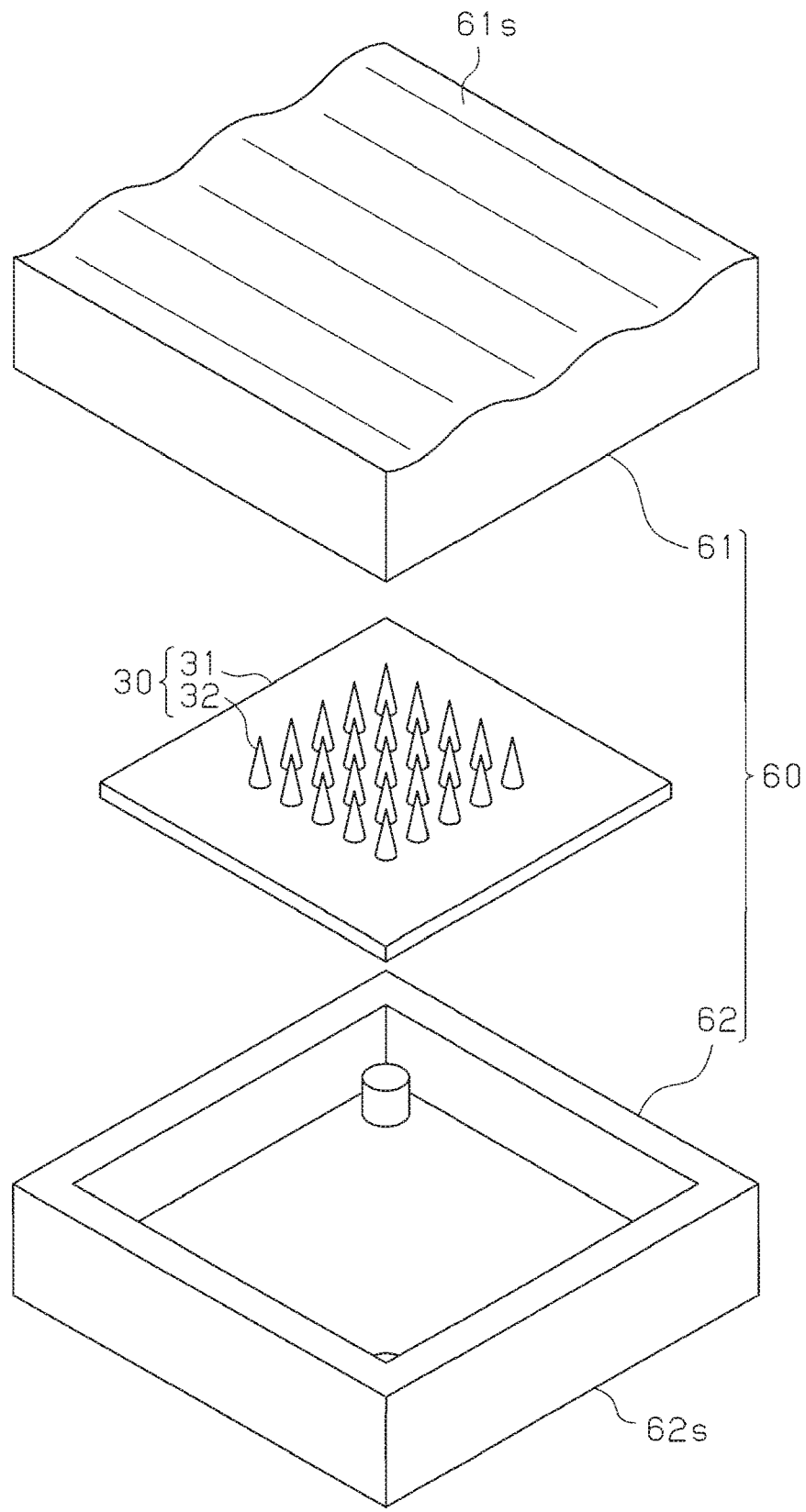
FIG. 23 is an exploded perspective view which shows an exploded perspective configuration of the microneedle unit according to the second embodiment.

As show in FIG. 23, the outer shape of the cover 61 and the outer shape of the housing 62 may be different from each other. For example, while the housing outer surface 62s of the housing 62 is a flat surface, the cover outer surface 61s of the cover 61 may include a flat surface and a surface having a predetermined shape such as a stepped surface. Accordingly, compared with the configuration in which the outer shape of the cover 61 and the outer shape of the housing 62 are the same, the cover 61 and the housing 62 can be easily identified. Furthermore, those shapes allow the user to easily hold and handle the microneedle container.

Specifically, as show in FIG. 23, when the cover 61 has a configuration having a stepped surface, the user of the microneedle unit 10 has difficulty in handling of the microneedle unit 10 with the cover 61 facing down. That is, the user has difficulty in handling of the microneedle unit 10 in the state that the housing 62 is stacked on the cover 61. Accordingly, the user can easily handle the microneedle container 60 without making mistakes regarding the up and down orientation of the microneedle container 60, and does not need to care about the up and down orientation of the microneedle container 60.

Further, since the outer shape of the cover 61 and the outer shape of the housing 62 are different from each other, the design of the outer appearance of the microneedle container 60 can be improved by interaction of the outer shape of the cover 61 and the outer shape of the housing 62.

The microneedle container 60 may be manufactured by a method such as injection molding, extrusion, use of a 3D printer, cutting, laser processing or the like. The cover 61 and the cover protruding member 61a may be integrally formed, or the cover protruding member 61a and the cover 61 may be joined together by a given method after they are separately formed. Further, similarly to the cover 61 and the cover protruding member 61a, the housing 62 and the housing protruding member 62a may be integrally formed, or the housing 62 and the housing protruding member 62a may be joined together by a given method after they are separately formed.

EXAMPLES

Examples and comparative examples of the microneedle unit 10 and microneedle container 60 will be described below.

Example 1

By using micromachining technology, projections each having a regular square pyramid shape with a height of 120 μm and a base side length of 38 μm were formed on the silicon substrate. One hundred projections were arranged on the silicon substrate in a matrix of 10 columns and 10 lines with an interval of 1 mm with the adjacent projections. Accordingly, 100 projections were disposed in the projection forming section, which is a square with a side length of approximately 9 mm.

Then, a pattern was transferred while inverting the protrusion and recess of projection of the microneedle by using an ethylene vinyl acetate copolymer resin to form an intaglio plate made of an ethylene vinyl acetate copolymer resin.

After hydroxypropyl cellulose was dissolved in water, hydroxypropyl cellulose solution was deaerated under a vacuum environment to prepare a material for forming the microneedle. The hydroxypropyl cellulose solution had a concentration of hydroxypropyl cellulose of 5 wt %.

The prepared hydroxypropyl cellulose solution was supplied to the intaglio plate made of ethylene vinyl acetate copolymer resin by using an ink jet method to fill a recess of the intaglio plate. Then, the hydroxypropyl cellulose solution was left in an environment of a temperature of 20° C. and a relative humidity of 60% for drying. The dried hydroxypropyl cellulose was removed from the intaglio plate to obtain a microneedle. The obtained microneedle had a base thickness of 1 mm.

Further, recess-shaped containers made of polyacetal were provided as the cover and the housing. Each container was formed in a bottomed tubular shape with a length of 5 mm between the inner surface at the bottom of the recess-shaped container and the open tubular end. Protruding members made of urethane, each having a columnar shape with a height of 5 mm and a width of 3 mm, were disposed at two opposing corners on the diagonal line on each of the inner surface of the cover bottom of the cover and the inner surface of the housing bottom of the housing. The cover protruding members on the cover and the housing protruding members on the housing were disposed at positions that overlap each other as seen in the stacking direction of the housing and the cover. Thus, the microneedle container including the cover having two cover protruding members and the housing having two housing protruding members were fabricated.

The microneedle was disposed in the housing so that the housing protruding members of the housing were positioned on the supported surface of the base. Then, the cover was brought into contact with the housing in the state that the cover protruding members of the cover each oppose the housing protruding members of the housing in the extending direction. In so doing, it was observed that the distal end of the cover protruding members were deformed when the cover protruding members were pushed against the abutted section of the projection forming surface of the base, and the distal end of the housing protruding members were deformed when the housing protruding members were pushed against the supported surface of the base.

The microneedle container that houses the microneedle was held by hand and vibration in the extending direction of the projection was applied to the microneedle container for a period of one minute. The result showed that the microneedle was held at the same position to the microneedle container as the position before the vibration was applied to the microneedle container. Further, it was found that opening of the microneedle container by separating the housing and the cover and closing of the microneedle container by attaching the housing and the cover are both possible. Moreover, the projection of the microneedle was observed by using a microscope. It was found that the distal end of the projection held the sharpness, thereby preventing deformation of the projection.

Example 2

The microneedle was fabricated by the same method as Example 1.

Further, the same recess-shaped containers as Example 1 made of polyacetal were provided as the cover and the housing. Protruding members made of urethane, each having a columnar shape with a height of 4.5 mm and a width of 3 mm, were disposed at two opposing corners on the diagonal line on each of the inner surface of the cover bottom of the cover and the inner surface of the housing bottom of the housing. The cover protruding members on the cover and the housing protruding members on the housing were disposed at positions that overlap each other as seen in the stacking direction of the housing and the cover. Thus, the microneedle container including the cover having two cover protruding members and the housing having two housing protruding members were fabricated.

The microneedle was disposed in the housing so that the housing protruding members of the housing were positioned on the supported surface of the base. Then, the cover was brought into contact with the housing in the state that the cover protruding members of the cover each oppose the housing protruding members of the housing in the extending direction. In so doing, it was observed that the housing protruding member is in contact with the supported surface of the base, and the cover protruding member is in contact with the abutted section of the projection forming surface of the base.

The microneedle container that houses the microneedle was held with a hand and a strong vibration in the up and down direction, which is the extending direction of the projection, and in the right and left direction, which is the arrangement direction of the projection, was applied to the microneedle container for a period of one minute. The result showed that the microneedle was held at the same position to the microneedle container as the position before the vibration was applied to the microneedle container. Further, it was found that opening of the microneedle container by separating the housing and the cover and closing of the microneedle container by attaching the housing and the cover are both possible. Moreover, the projection of the microneedle was observed by using a microscope. It was found that the distal end of the projection held the sharpness, thereby preventing deformation of the projection.

Example 3

The microneedle was fabricated by the same method as Example 1.

Further, the same recess-shaped containers as Example 1 made of polyacetal were provided as the cover and the housing. Protruding members made of urethane, each having a columnar shape with a height of 4.5 mm and a width of 3 mm, were disposed at two opposing corners on the diagonal line on the inner surface of the cover bottom of the cover. Then, protruding members made of urethane, each having a columnar shape with a height of 4.4 mm and a width of 3 mm, were disposed at two opposing corners on the inner surface of the housing bottom of the housing. The cover protruding members on the cover and the housing protruding members on the housing were disposed at positions that overlap each other as seen in the stacking direction of the housing and the cover. Thus, the microneedle container including the cover having two cover protruding members and the housing having two housing protruding members were fabricated.

The microneedle was disposed in the housing so that the housing protruding members of the housing were positioned on the supported surface of the base. Then, the cover was brought into contact with the housing in the state that the cover protruding members of the cover each oppose the housing protruding members of the housing in the extending direction. In so doing, it was observed that the housing protruding member is in contact with the supported surface of the base, while the cover protruding member is not in contact with the base. Furthermore, a distance between the distal end of the cover protruding member and the distal end of the housing protruding member was 1.1 mm, which is smaller than the sum of a thickness of the base and the length of the projection of the microneedle.

The microneedle container that houses the microneedle was held by hand and vibration in the extending direction of the projection was applied to the microneedle container for a period of one minute. The result showed that the microneedle was held at the same position to the microneedle container as the position before the vibration was applied to the microneedle container. Further, it was found that opening of the microneedle container by separating the housing and the cover and closing of the microneedle container by attaching the housing and the cover are both possible. Moreover, the projection of the microneedle was observed by using a microscope. It was found that the distal end of the projection held the sharpness, thereby preventing deformation of the projection.

Comparative Example 1

The microneedle was fabricated by the same method as Example 1.

Further, the same recess-shaped containers as Example 1 made of polyacetal were provided as the cover and the housing. Protruding members made of urethane, each having a columnar shape with a height of 3 mm and a width of 3 mm, were disposed at two opposing corners on the diagonal line on each of the inner surface of the cover bottom of the cover and the inner surface of the housing bottom of the housing. The cover protruding members on the cover and the housing protruding members on the housing were disposed at positions that overlap each other as seen in the stacking direction of the housing and the cover. Thus, the microneedle container including the cover having two cover protruding members and the housing having two housing protruding members were fabricated.

The microneedle was disposed in the housing so that the housing protruding members of the housing were positioned on the supported surface of the base. Then, the cover was brought into contact with the housing in the state that the cover protruding members of the cover each oppose the housing protruding members of the housing in the extending direction. In so doing, it was observed that the housing protruding member is in contact with the supported surface of the base, while the cover protruding member is not in contact with the base. Furthermore, a distance between the distal end of the cover protruding member and the distal end of the housing protruding member was 4 mm, which is larger than the sum of a thickness of the base and the length of the projection of the microneedle.

The microneedle container that houses the microneedle was held by hand and vibration in the extending direction of the projection was applied to the microneedle container for a period of one minute. The result showed that the microneedle was displaced to the microneedle container and was moved to a position at which the projection was brought into contact with the cover protruding member. Moreover, the projection of the microneedle was observed by using a microscope. It was found that the distal end of the projection was bent in a direction crossing with the extending direction.

As described above, according to the microneedle unit and the microneedle container of the second embodiment, the following effect can be achieved in addition to the effect obtained in the first embodiment.

(4) When the above formula 1 is satisfied, the cover protruding member 61a and the housing protruding member 62a are each in contact with the base 31 of the microneedle 30 as the microneedle 30 is housed in the microneedle container 60. As a consequence, if the microneedle container 60 is subject to vibration in the extending direction, the microneedle 30 is prevented from being easily displaced in the extending direction. Accordingly, the projection 32 of the microneedle 30 can be less likely to be deformed.

(5) When at least one of the cover protruding member 61a and the housing protruding member 62a is an elastic member, the elastic member is pressed against the base 31 of the microneedle 30 as the cover 61 and the housing 62 are in contact with each other. Since the microneedle 30 of the microneedle container 60 is less likely to be displaced, the projection 32 of the microneedle 30 is less likely to be deformed in the microneedle container 60 is subject to vibration in the extending direction.

(6) When the cover 61 and the housing 62 are in the same shape, manufacturing of the microneedle container 60 is easy compared with the configuration in which the cover and the housing have the different shapes from each other.

(7) When the outer shape of the cover 61 and the outer shape of the housing 62 are different from each other, the cover 61 and the housing 62 can be easily identified compared with the configuration in which the outer shape of the cover 61 and the outer shape of the housing 62 are the same.

<Modification Examples of Second Embodiment>

Figure 30A:
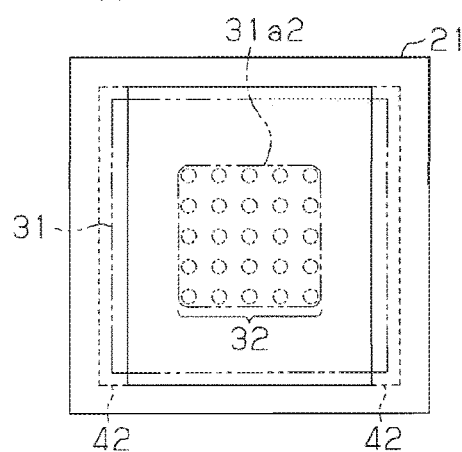
FIG. 30(a) is a plan view which shows a plan configuration of the cover as seen from the cover bottom according to the modification example.

The above second embodiment may be appropriately modified as below. FIGS. 24(a), 25(a), 26(a), 27(a) and 28(a) are plan views similar to FIG. 14, and show a plan configuration of the cover 61 of the microneedle container 60 as seen from the cover bottom 72 of the cover 61. Further, FIGS. 24(b), 25(b), 26(b), 27(b), 28(b) and 30(b) are plan views similar to FIG. 15, and show a plan configuration of the housing 62 of the microneedle container 60 as seen from the housing bottom 82 of the housing 62. FIG. 30(a) is a plan view similar to FIG. 3, and shows a plan configuration of the cover 21 as seen from the wall surface having the cover facing surface 44.

In FIGS. 24(a), 25(a), 26(a), 27(a) and 28(a), for the convenience of explanation of the arrangement of the cover protruding member 61a of the cover 61, the cover bottom 72 is not illustrated. Further, in FIGS. 24(b), 25(b), 26(b), 27(b), 28(b) and 30(b), for the convenience of explanation of the arrangement of the housing protruding member 62a of the housing 62, the housing bottom 82 is not illustrated. In FIG. 30(a), for the convenience of explanation of the arrangement on the abutment surface 42 of the cover 21, the wall surface having the cover facing surface 44 is not illustrated, and the abutment surface 42 formed on the cover 21 is illustrated by the dotted line.

Figure 24A:
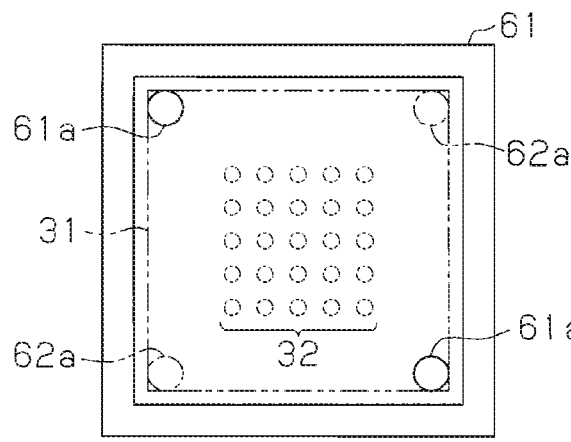
FIG. 24(a) is a plan view which shows a plan configuration of the cover as seen from the cover bottom according to a modification example.
Figure 24B:
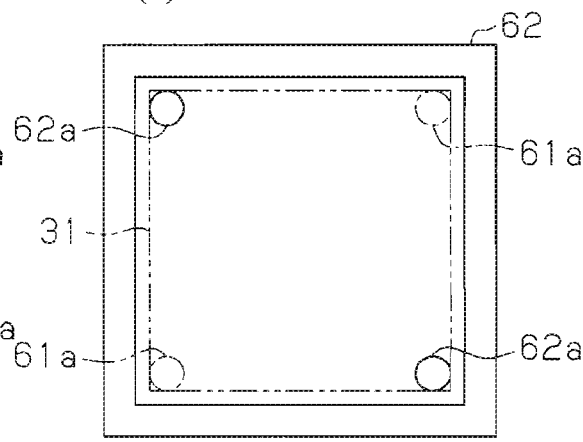
FIG. 24(b) is a plan view which shows a plan configuration of the housing as seen from the housing bottom according to a modification example.

With reference to FIG. 24, the positions of the cover protruding member 61a and housing protruding member 62a as seen in the stacking direction of the housing 62 and the cover 61 will be described. In FIG. 24(a), the position of the housing protruding member 62a when the microneedle container 60 is assembled is indicated by the two-dot chain line, and in FIG. 24(b), the position of the cover protruding member 61a when the microneedle container 60 is assembled is indicated by the two-dot chain line.

As shown in FIG. 24(a), similarly to the cover 61 shown in FIG. 14, one of two cover protruding members 61a of the cover 61 is located at a corner on the inner surface of the cover bottom 72, and the other of two cover protruding members 61a is located at a corner on the diagonal line which passes through the corner on which the one of the cover protruding members 61a is located.

On the other hand, as shown in FIG. 24(b), one of two housing protruding members 62a of the housing 62 is located at a corner on the inner surface of the housing bottom 82, and the other of two housing protruding members 62a is located at a corner on the diagonal line which passes through the corner on which the one of the housing protruding members 62a is located. The two housing protruding members 62a shown in FIG. 24(b) are located on the inner surface of the housing bottom 82 on the diagonal line that crosses the diagonal line on which the two housing protruding member 62a shown in FIG. 15 are located.

Accordingly, the position of the cover 61 and the position of the housing 62 do not overlap each other as seen in the stacking direction of the cover 61 and the housing 62 when the microneedle container 60 is assembled. That is, each of the cover protruding members 61a does not face the housing protruding member 62a with the microneedle 30 housed in the microneedle container 60 interposed therebetween.

Figure 25A:
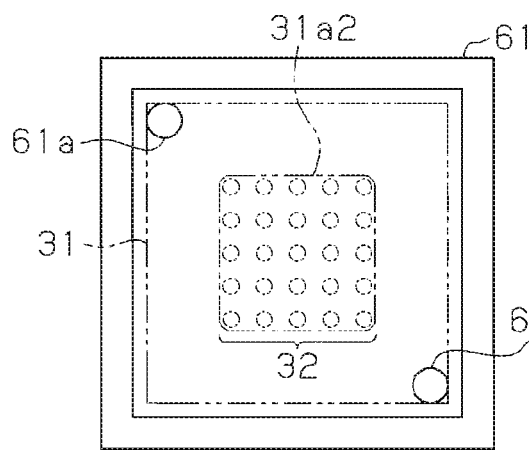
FIG. 25(a) is a plan view which shows a plan configuration of the cover as seen from the cover bottom according to a modification example.

As shown in FIG. 25(a), similarly to the cover 61 shown in FIG. 14, one of two cover protruding members 61a of the cover 61 is located at a corner on the inner surface of the cover bottom 72, and the other of two cover protruding members 61a is located at a corner on the diagonal line which passes through the corner on which the one of the cover protruding members 61a is located.

Figure 25B:
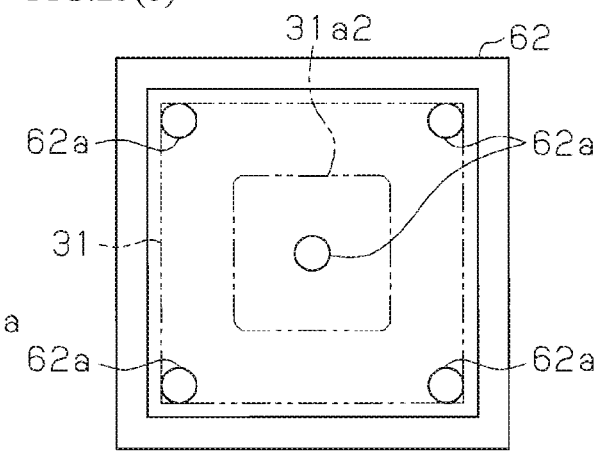
FIG. 25(b) is a plan view which shows a plan configuration of the housing as seen from the housing bottom according to the modification example.

On the other hand, as shown in FIG. 25(b), the housing 62 includes five housing protruding members 62a. Four of the five housing protruding members 62a are each located at different corners on the inner surface of the housing bottom 82. One housing protruding member 62a is located substantially at the center on the inner surface of the housing bottom 82 at a position that faces the back surface of the projection forming section 31a2 of the base 31.

When the microneedle container 60 is assembled, each of the positions of two housing protruding members 62a overlaps the position of one cover protruding member 61a as seen in the stacking direction of the cover 61 and the housing 62. On the other hand, each of the positions of three housing protruding members 62a does not overlap the position of the cover protruding member 61a as seen in the stacking direction of the cover 61 and the housing 62.

As described above, the housing 62 may include three or more housing protruding members 62a, and not only the housing 62, the cover 61 also may include three or more cover protruding members 61a.

Figure 26A:
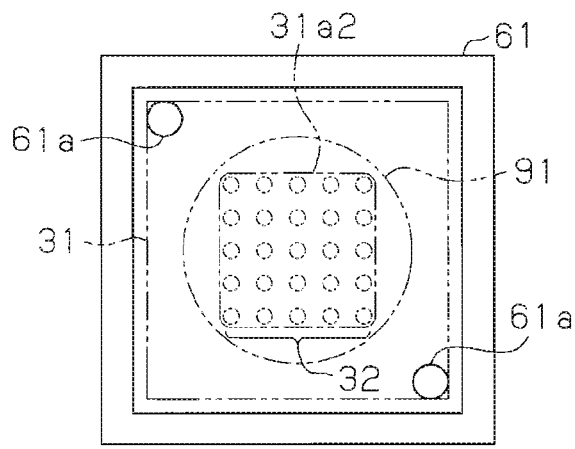
FIG. 26(a) is a plan view which shows a plan configuration of the cover as seen from the cover bottom according to the modification example.

As shown in FIG. 26(a), similarly to the cover 61 shown in FIG. 14, one of two cover protruding members 61a of the cover 61 is located at a corner on the inner surface of the cover bottom 72, and the other of two cover protruding members 61a is located at a corner on the diagonal line which passes through the corner on which the one of the cover protruding members 61a is located.

Figure 26B:
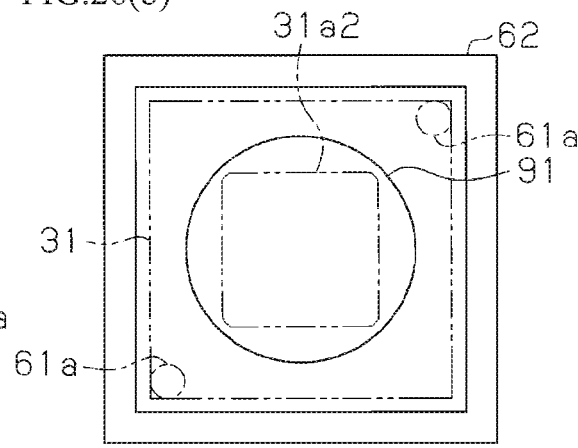
FIG. 26(b) is a plan view which shows a plan configuration of the housing as seen from the housing bottom according to the modification example.

On the other hand, as shown in FIG. 26(b), the housing 62 includes one housing protruding member 91, and the one housing protruding member 91 is located substantially at the center on the inner surface of the housing bottom 82 at a position that faces the back surface of the projection forming section 31a2 of the base 31. The diameter of the housing protruding member 91 is smaller than the distance between two cover protruding members 61a.

Accordingly, the position of one housing protruding member 91 does not overlap the position of either of two cover protruding members 61a as seen in the stacking direction of the cover 61 and the housing 62 when the microneedle container 60 is assembled.

As described above, the housing 62 may include only one housing protruding member 91, and not only the housing 62, the cover 61 may also include only one cover protruding member 61a.

Figure 27A:
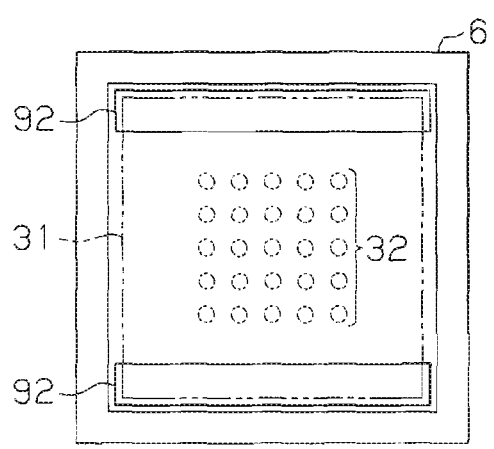
FIG. 27(a) is a plan view which shows a plan configuration of the cover as seen from the cover bottom according to the modification example.

As shown in FIG. 27(a), the cover 61 includes two cover protruding members 92, and each of the cover protruding members 92 may have a cuboid shape that extends on one side of the outer edge of the cover bottom 72. The two cover protruding members 92 each extend, for example, on each of two sides, which are parallel to each other, of four sides of the outer edge of the cover bottom 72.

Figure 27B:
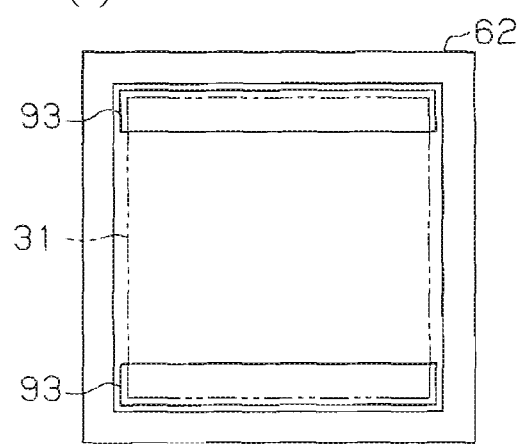
FIG. 27(b) is a plan view which shows a plan configuration of the housing as seen from the housing bottom according to the modification example.

On the other hand, as shown in FIG. 27(b), the housing 62 includes two housing protruding members 93, and each of the housing protruding member 93 has a cuboid shape that extends on two sides of the outer edge of the housing bottom 82. The two housing protruding members 93 each extend, for example, on each of two sides, which are parallel to each other, of four sides of the outer edge of the housing bottom 82.

When the microneedle container 60 is assembled, each of the positions of two housing protruding members 93 overlaps each of the positions of the cover protruding members 92 as seen in the stacking direction of the cover 61 and the housing 62.

Further, each of the positions of two cover protruding members 92 may not necessarily overlap each of the positions of the housing protruding member 93 as seen in the stacking direction of the cover 61 and the housing 62. The two cover protruding members 92 may extend on each of two sides, which are not parallel to each other, of four sides of the outer edge of the cover bottom 72. The two housing protruding members 93 may also extend on each of two sides, which are not parallel to each other, of four sides of the outer edge of the housing bottom 82.

Figure 28A:
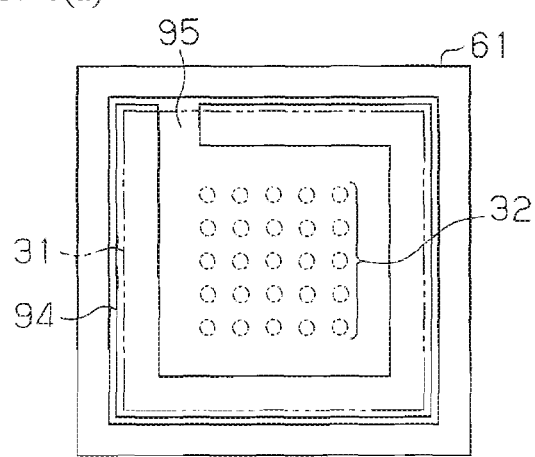
FIG. 28(a) is a plan view which shows a plan configuration of the cover as seen from the cover bottom according to the modification example.
Figure 28B:
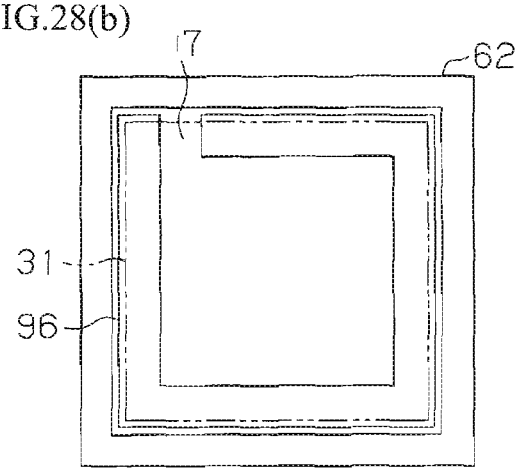
FIG. 28(b) is a plan view which shows a plan configuration of the housing as seen from the housing bottom according to the modification example.

As shown in FIG. 28(a), when the cover 61 includes one cover protruding member 94, the cover protruding member 94 may have an ended annular shape that extends on part of the outer edge of the cover bottom 72. In the cover protruding member 94, a spaced section 95 is formed between two ends. Further, when the housing 62 includes one housing protruding member 96, the housing protruding member 96 may have an ended annular shape that extends on part of the outer edge of the housing bottom 82, similarly to the cover protruding member 94. In the housing protruding member 96, a spaced section 97 is formed between two ends.

When the microneedle container 60 is assembled, the position of the spaced section 95 in the cover 61 and the position of the spaced section 97 in the housing 62 do not overlap each other as seen in the stacking direction of the cover 61 and the housing 62, although they almost entirely overlap each other.

Further, the position of the spaced section 95 in the cover 61 and the position of the spaced section 97 in the housing 62 may overlap each other as seen in the stacking direction of the cover 61 and the housing 62, although they almost entirely overlap each other. The cover protruding member 94 and the housing protruding member 96 may also have an endless annular shape.

Figure 29:
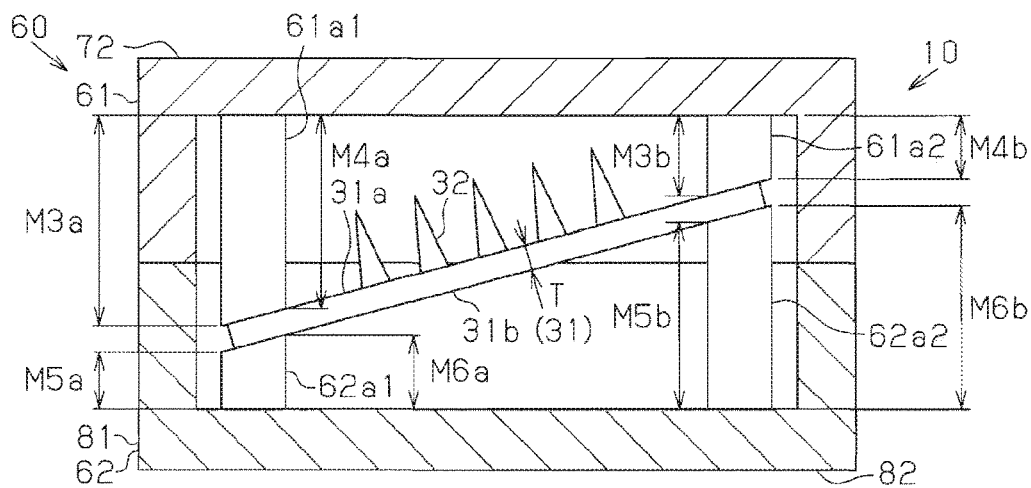
FIG. 29 is a cross sectional view which shows a cross sectional configuration of the microneedle unit according to the modification example.

In the microneedle container 60 shown in FIG. 21, the shapes of the first cover protruding member 61a1, the second cover protruding member 61a2, the first housing protruding member 62a1 and the second housing protruding member 62a2 may be modified as shown in FIG. 29.

That is, as shown in FIG. 29, the cover 61 includes the first cover protruding member 61a1 and the second cover protruding member 61a2, and the length of the first cover protruding member 61a1 is larger than the length of the second cover protruding member 61a2. On the other hand, the housing 62 includes the first housing protruding member 62a1 and the second housing protruding member 62a2, and the length of the first housing protruding member 62a1 is smaller than the length of the second housing protruding member 62a2.

Each of the distal end of the first cover protruding member 61a1 and the distal end of the second cover protruding member 61a2 are formed by an inclined surface that is inclined to the cover bottom 72 by a predetermined angle. On the other hand, each of the distal end of the first housing protruding member 62a1 and the distal end of the second housing protruding member 62a2 are formed by an inclined surface that is inclined to the housing bottom 82 by a predetermined angle.

In the first cover protruding member 61a1, a maximum length of a maximum portion is a first cover protruding member maximum length M3a, and a minimum length of a minimum portion is a first cover protruding member minimum length M4a. In the second cover protruding member 61a2, a maximum length of a maximum portion is a second cover protruding member maximum length M3b, and a minimum length of a minimum portion is a second cover protruding member minimum length M4b.

On the other hand, in the first housing protruding member 62a1, a minimum length of a minimum portion is a first housing protruding member minimum length M5a, and a maximum length of a maximum portion is a first housing protruding member maximum length M6a. In the second housing protruding member 62a2, a minimum length of a minimum portion is a second housing protruding member minimum length M5b, and a maximum length of a maximum portion is a second housing protruding member maximum length M6b.

When the microneedle container 60 is assembled, the position of the first cover protruding member 61a1 and the position of the first housing protruding member 62a1 overlap each other and the position of the second cover protruding member 61a2 and the position of the second housing protruding member 62a2 overlap each other as seen in the stacking direction of the housing 62 and the cover 61. Further, in the first cover protruding member 61a1 and in the first housing protruding member 62a1, the position of the maximum portion of the first cover protruding member 61a1 and the position of the minimum portion of the first housing protruding member 62a1 overlap each other, and the position of the minimum portion of the first cover protruding member 61a1 and the position of the maximum portion of the first housing protruding member 62a1 overlap each other. Further, in the second cover protruding member 61a2 and the second housing protruding member 62a2, the position of the maximum portion of the second cover protruding member 61a2 and the position of the minimum portion of the second housing protruding member 62a2 overlap each other, and the position of the minimum portion of the second cover protruding member 61a2 and the position of the maximum portion of the second housing protruding member 62a2 overlap each other.

Each of the distal end of the first cover protruding member 61a1 and the distal end of the second cover protruding member 61a2 are formed by an inclined surface that is inclined to the cover bottom 72 by a predetermined angle ×1. On the other hand, each of the distal end of the first housing protruding member 62a1 and the distal end of the second housing protruding member 62a2 are formed by an inclined surface that is inclined to the housing bottom 82 by a predetermined angle ×2. When each of the inclined surface of the first cover protruding member 61a1 and the inclined surface of the second cover protruding member 61a2 are on the projection forming surface of the base 31, and the inclined surface of the first housing protruding member 62a1 and the inclined surface of the second housing protruding member 62a2 are on the supported surface 31b of the base 31.

Here, the first cover protruding member maximum length M3a, the first cover protruding member minimum length M4a, the second cover protruding member maximum length M3b, the second cover protruding member minimum length M4b, the first housing protruding member minimum length M5a, the first housing protruding member maximum length M6a, the second housing protruding member minimum length M5b, the second housing protruding member maximum length M6b and the thickness T of the base 31 satisfy the following formula 6 and formula 7.

$$(M3a + M5a + T/\cos(\times 1)) = (M4a\ M6a + T/\cos(\times 1)) \quad \text{(Formula 6)}$$

$$(M3b + M5b\ T/\cos(\times 2)) = (M4b + M6b + T/\cos(\times 2)) \quad \text{((Formula 7)}$$

Further, in the cover 61, the distal end of the first cover protruding member 61a1 in the maximum portion, the distal end of the first cover protruding member 61a1 in the minimum portion, the distal end of the second cover protruding member 61a2 in the maximum portion and the distal end of the second cover protruding member 61a2 in the minimum portion are located on a cover straight line, which is a single straight line. Further, in the housing 62, the distal end of the first housing protruding member 62a1 in the minimum portion, the distal end of the first housing protruding member 62a1 in the maximum portion, the distal end of the second housing protruding member 62a2 in the minimum portion and the distal end of the second housing protruding member 62a2 in the maximum portion are located on a housing straight line, which is a single straight line. The cover straight line and the housing straight line are parallel to each other, and the distance between the cover straight line and the housing straight line in the extending direction is equal to the thickness T of the base 31.

Accordingly, when the microneedle 30 is housed in the microneedle container 60, the base 31 of the microneedle 30 forms a predetermined angle to the housing bottom 82. As a consequence, when the microneedle 30 is housed in the microneedle container 60, the microneedle 30 is easily taken out compared with the configuration in which the base 31 of the microneedle 30 and the housing bottom 82 are parallel to each other.

Further, the distal end of the first cover protruding member 61a1 and the distal end of the second cover protruding member 61a2 are arranged on the projection forming surface 31a of the microneedle 30, and the distal end of the first housing protruding member 62a1 and the distal end of the second housing protruding member 62a2 are arranged on the supported surface 31b of the microneedle 30. As a result, the position of the microneedle 30 to the microneedle container 60 is less likely to be displaced.

The cover 61 in the second embodiment and the modification example of the second embodiment may also have a cover bulging portion which bulges outward from the outer periphery of the cover 61, similarly to the modification example of the first embodiment. Further, the housing 62 may also include a housing bulging portion that bulges outward from the outer periphery of the housing 62 as in the modification example of the first embodiment. With this configuration, a similar effect to the modification example of the first embodiment can also be obtained.

The microneedle 30 housed in the microneedle container 60 in the second embodiment and the modification example of the second embodiment may be the microneedle 30 having the notch 33 in the abutted section 31a1 of the base 31, similarly to the modification example. With this configuration, a similar effect to the modification example of the first embodiment can also be obtained.

The cover described in the second embodiment and the modification example of the second embodiment can be appropriately combined with the housing described in the second embodiment and the modification example of the second embodiment.

Figure 30B:
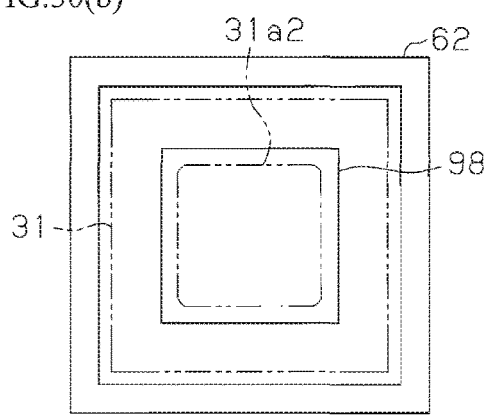
FIG. 30(b) is a plan view which shows a plan configuration of the housing as seen from the housing bottom according to the modification example.

As shown in FIG. 30(a), the cover 21 includes two abutment surfaces 42 that abut the microneedle 30, similarly to the cover 21 shown in FIG. 3. On the other hand, as shown in FIG. 30(b), the housing includes one housing protruding member 98. The housing protruding member 98 has a rectangular columnar shape and is located substantially at the center on the inner surface of the housing bottom 82 at a position that faces the back surface of the projection forming section 31a2 of the base 31 of the microneedle 30.

When the microneedle container is assembled, the position of part of the abutment surface 42 and part of the housing protruding member 98 do not overlap each other as seen in the stacking direction of the cover 21 and the housing 62.

As described above, in the microneedle container, the cover 21 in the first embodiment and the modification example of the first embodiment and the housing 62 in the second embodiment and the modification example of the second embodiment can be appropriately combined. Further, the cover 61 in the second embodiment and the modification example of the second embodiment and the housing 22 in the first embodiment and the modification example of the first embodiment can be appropriately combined.

<Other Modification Examples>

The configuration of the microneedle 30 described in the first embodiment and the second embodiment may be modified as follows.

Figure 31:
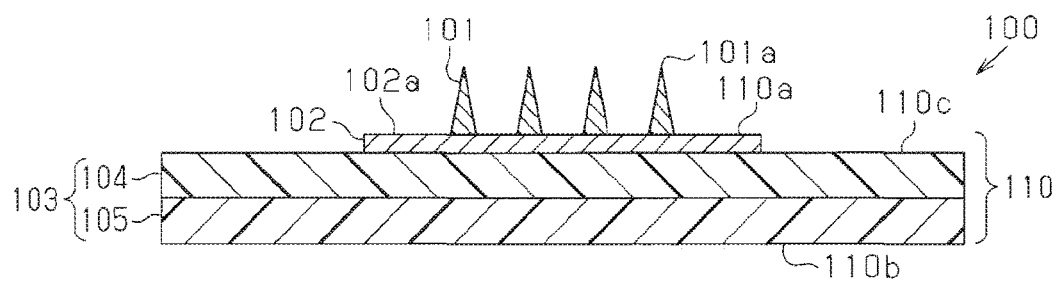
FIG. 31 is a cross sectional view which shows a cross sectional configuration of the microneedle according to the modification example.

As shown in FIG. 31, the microneedle 100 may include a plurality of projections 101, a projection forming section 102 and an adhesive sheet 103. The projection forming section 102 has a plate shape having a forming surface 102a on which a plurality of projections 101 are formed, and the adhesive sheet 103 is adhered to a surface of the projection forming section 102 opposite to the forming surface 102a. The adhesive sheet 103 also has a plate shape larger than the projection forming section 102, and includes an adhesive layer 104 adhered to the projection forming section 102, and a base sheet 105 that supports the adhesive layer 104.

The adhesive layer 104 is attached to the skin to hold the microneedle 100 on the skin when the microneedle 100 is pierced into the skin. The adhesive sheet 103 may be adhered to the periphery of the projection forming section 102, and the adhesive layer 104 may be exposed to the outside of the periphery of the projection forming section 102 so that it is attached to the skin when the microneedle is pierced into the skin.

In the microneedle 100, the projection forming section 102 and the adhesive sheet 103 constitute a base 110 of the microneedle 100. In the base 110, a projection forming surface 110a having a stepped surface is formed by the forming surface 102a of the projection forming section 102 and a portion of the adhesive layer 104 adhered to the projection forming section 102 and is not covered by the projection forming section 102. In the base 110, a supported surface 110b is a surface opposite to the projection forming surface 110a, that is, a surface of the base sheet 105 which is opposite to the surface which is in contact with the adhesive layer 104.

In the projection forming surface 110a, an abutted section 110c is a portion of the adhesive layer 104 which does not contain the projections 101, in other words, which surrounds a plurality of projections 101.

When the microneedle 100 is housed in the microneedle container 20, 60, the abutted section 110c faces the abutment section of the microneedle container 20, 60, while the supported surface 110b is supported by the supporting section of the microneedle container 20, 60.

When the microneedle container 20, 60 is housed in the microneedle 100, a distance between the abutment section and the facing section of the microneedle container 20, 60 may be larger than a distance between the abutted section 110c and the distal end 101a of the projection 101. Further, in the microneedle container 20, 60, a distance between the abutment section and the supporting section may be smaller than the sum of a distance between the abutted section 110c and the supported surface 110b in the extending direction and a distance between the abutted section 110c and the distal end 101a of the projection 101.

Figure 32:
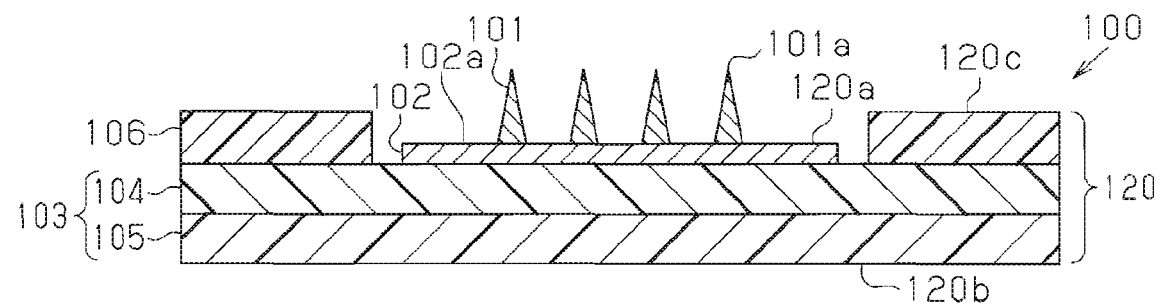
FIG. 32 is a cross sectional view which shows a cross sectional configuration of the microneedle according to the modification example.

As shown in FIG. 32, the microneedle 100 may have a configuration, as well as the configuration described in connection to FIG. 31, which includes a peeling sheet 106 that covers a portion of the adhesive layer 104 which is not covered by the projection forming section 102. The peeling sheet 106 is located on a surface of the adhesive sheet 103 opposite to the base sheet 105 and surrounds the projection forming section 102.

In the microneedle 100, the projection forming section 102, the adhesive sheet 103 and the peeling sheet 106 constitute a base 120. In the base 120, a projection forming surface 120a is formed by the forming surface 102a of the projection forming section 102, a surface of the peeling sheet 106 opposite to the adhesive sheet 103 and a portion of the adhesive sheet 103 which is not covered by the projection forming section 102 and the peeling sheet 106. In the base 120, a supported surface 120b is a surface of the base sheet 105 which is opposite to the surface which is in contact with the adhesive layer 104.

In the projection forming surface 120a, an abutted section 120c is a portion of the peeling sheet 106 which does not contain the projections 101, in other words, which surrounds a plurality of projections 101.

When the microneedle 100 is housed in the microneedle container 20, 60, the abutted section 120c faces the abutment section of the microneedle container 20, 60, while the supported surface 120b is supported by the supporting section of the microneedle container 20, 60.

When the microneedle container 20, 60 is housed in the microneedle 100, a distance between the abutment section and the facing section of the microneedle container 20, 60 may be larger than a distance between the abutted section 120c and the distal end 101a of the projection 101. Further, in the microneedle container 20, 60, a distance between the abutment section and the supporting section may be smaller than the sum of a distance between the abutted section 120c and the supported surface 120b in the extending direction and a distance between the abutted section 120c and the distal end 101a of the projection 101.

Figure 33:
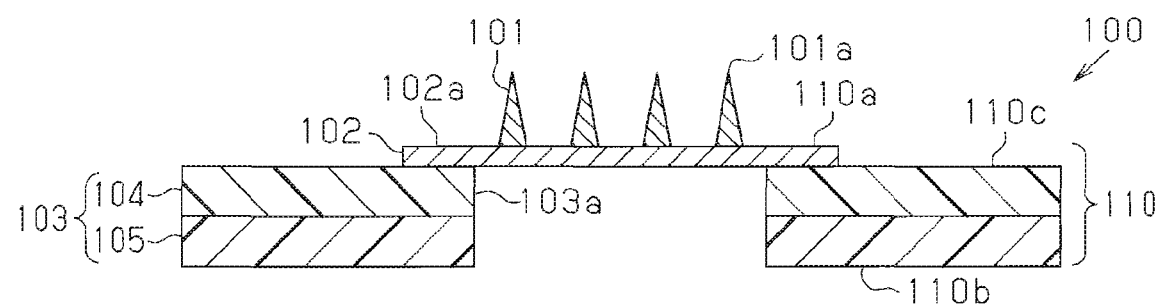
FIG. 33 is a cross sectional view which shows a cross sectional configuration of the microneedle according to the modification example.

As shown in FIG. 33, in the microneedle 100 shown in FIG. 31, the adhesive sheet 103 may include an opening 103a that exposes the projection forming section 102 as seen in the direction facing the base sheet 105. The opening 103a may be a hole formed in the adhesive sheet 103 or a slit extending along the adhesive sheet 103. For example, the opening 103a overlaps the projection 101 as seen in the direction facing the projection 101. Further, the adhesive sheet 103 may be adhered to the periphery of the projection forming section 102, and the adhesive layer 104 may be exposed to the outside the periphery so that it is attached to the skin when the microneedle 100 is pierced into the skin. That is, the adhesive layer 104 may be exposed to the outside of the periphery on the entire periphery of the projection forming section 102, or may be exposed to the outside of the periphery on part of the periphery of the projection forming section 102.

Figure 34:
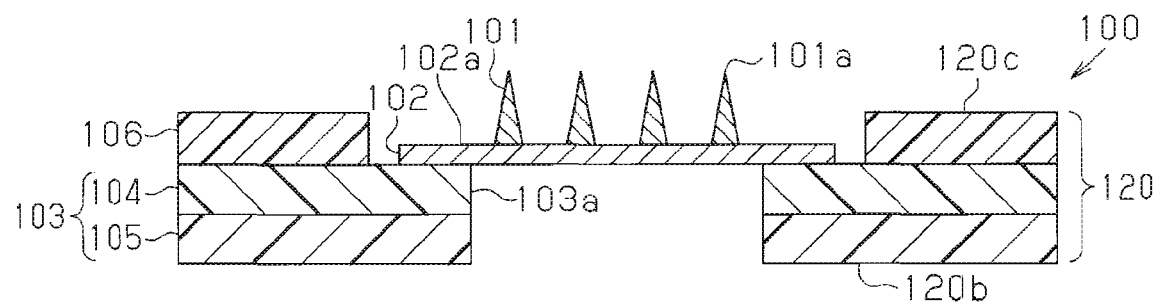
FIG. 34 is a cross sectional view which shows a cross sectional configuration of the microneedle according to the modification example.

As shown in FIG. 34, in the microneedle 100 shown in FIG. 32, the adhesive sheet 103 may include an opening 103a that exposes the projection forming section 102 as seen in the direction facing the base sheet 105. The opening 103a may be a hole formed in the adhesive sheet 103 or a slit extending along the adhesive sheet 103. For example, the opening 103a overlaps the projection 101 as seen in the direction facing the projection 101. Further, the adhesive sheet 103 may be adhered to the periphery of the projection forming section 102, and the adhesive layer 104 may be exposed to the outside the periphery so that it is attached to the skin when the microneedle 100 is pierced into the skin. That is, the adhesive layer 104 may be exposed to the outside of the periphery on the entire periphery of the projection forming section 102, or may be exposed to the outside of the periphery on part of the periphery of the projection forming section 102.

In a container having an inner wall having a stepped surface that supports the base of the microneedle, a distance between the stepped surface and an opening of the container which is closed by the cover is larger than the sum of a thickness of the base and a length of the projection.

Accordingly, when the microneedle is shipped along with the container and the container is exposed to vibration in the extending direction of the projection, the entire microneedle is displaced between To the stepped surface and the cover in the direction in which the stepped surface and the cover face each other. As a result, the projection of the microneedle may touch part of the inner wall of the container, which may cause the projection to be deformed into a shape inappropriate for piercing into the skin.

The technique of the present disclosure has an object to provide a microneedle unit and a microneedle container that prevent deformation of a projection when the microneedle container is subject to vibration in the extending direction of the projection.

An aspect of a microneedle unit of the technique of the present disclosure includes a microneedle and a microneedle container. The microneedle includes a base having a projection forming surface on which a projection is formed and a supported surface which is an opposite side to the projection forming surface, and a portion of the projection forming surface in which the projection is not provided is an abutted section. The microneedle container includes a housing that houses the microneedle and a cover that covers the microneedle housed in the housing. The housing includes a supporting section that supports the supported surface. The cover includes an abutment section that faces the abutted section, and a facing section that faces the projection, and a distance between the abutment section and the facing section is larger than a distance between the abutted section and a distal end of the projection in an extending direction in which the projection extends, and a distance between the abutment section and the supporting section is smaller than a sum of a distance between the abutted section and the supported surface and a distance between the abutted section and the distal end of the projection in the extending direction.

An aspect of a microneedle container of the technique of the present disclosure is a microneedle container that houses the microneedle, and the microneedle container is included in the above microneedle unit.

According to the above aspect, when the microneedle container is subject to vibration in the extending direction of the microneedle and the microneedle in the microneedle container is displaced, the projection of the microneedle is prevented from colliding with the facing section. In addition to that, the projection of the microneedle is less likely to be displaced into a gap between the abutment section and the supporting section. As a consequence, if the microneedle container is subject to vibration in a direction in which the projection extends, the microneedle is prevented from being easily deformed.

In another aspect of the microneedle unit of the technique of the present disclosure, it is preferable that an adhesive strength of the abutment section to the base and an adhesive strength of the supporting section to the base are different from each other.

According to another aspect of the microneedle unit of the technique of the present disclosure, a microneedle is easily held by one of the cover and the housing in the microneedle container when the microneedle container is opened. As a consequence, the microneedle can be easily taken out.

In another aspect of the microneedle unit of the technique of the present disclosure, each of the cover and the housing is a recess-shaped member, and the recess-shaped member includes an opening and a contact section that surrounds the opening. It is preferable that the contact section is in contact with the contact section of the other recess-shaped member, one of the abutment section and the supporting section is a close-contact section having a higher adhesive strength to the base than an adhesive strength of the other of the abutment section and the supporting section, one of the cover and the housing is a close-contact member having the close-contact section, and the close-contact section of the close-contact member is located inside the contact section and protrudes from the contact section in the extending direction.

According to another aspect of the microneedle unit of the technique of the present disclosure, the microneedle can be easily located on the close-contact section when the microneedle container is opened, and the microneedle on the close-contact section protrudes from the contact section.

In another aspect of the microneedle container of the technique of the present disclosure, the cover is a recess-shaped member which includes a cover tubular body having two cover tubular ends, and a cover bottom formed in a plate shape that closes one of the cover tubular ends, and the cover includes a cover protruding member which extends from the cover bottom to the opened cover tubular end, and the abutment section is disposed on the distal end of the cover protruding member. The housing includes a housing tubular body having two housing tubular ends, and a housing bottom formed in a plate shape that closes one of the housing tubular ends, and the housing includes a housing protruding member which extends from the housing bottom to the opened cover tubular end, and the supporting section is disposed on the distal end of housing protruding member. A length from an inner surface of the cover bottom to the opened cover tubular end is a cover length L1, a length from the cover bottom to the distal end of the cover protruding member is a cover protruding member length M1, a length from an inner surface of the housing bottom to the opened housing tubular end is a housing length L2, and a length from the housing bottom to the distal end is a housing protruding member length M2. Here, it is preferable to satisfy: (L1+L2)<+M2).

According to another aspect of the microneedle unit of the technique of the present disclosure, the cover protruding member and the housing protruding member are simultaneously in contact with the base of the microneedle when the microneedle is housed in the microneedle container. As a consequence, if the microneedle container is subject to vibration in the extending direction, the microneedle is prevented from being easily displaced in the extending direction. Accordingly, the projection of the microneedle can be less likely to be deformed.

In another aspect of the microneedle unit of the technique of the present disclosure, each of the cover and the housing includes an opening and a contact section that surrounds the opening. It is preferable that at least one of the cover protruding member and the housing protruding member is an elastic section having a length varying in the extending direction depending on whether the contact section of the cover and the contact section of the housing are in contact with each other, at least one of the cover and the housing is an elastic member having the elastic section, and the elasticity of the elastic section is higher than the elasticity of a portion of the elastic member other than the elastic section.

According to another aspect of the microneedle unit of the technique of the present disclosure, the elastic section is pressed against the base of the microneedle when the microneedle is housed in the microneedle container. Since the microneedle of the microneedle container is less likely to be displaced, the projection of the microneedle is less likely to be deformed in the microneedle container when subject to vibration in the extending direction.

According to a microneedle unit and a microneedle container of the technique of the present disclosure, deformation of a projection can be prevented if the microneedle container is subject to vibration in the extending direction of the projection.

REFERENCE SIGNS LIST

10 . . . microneedle unit,
20, 60 . . . microneedle container,
21, 61 . . . cover,
21a . . . abutment section,
21b, 61b . . . facing section,
22, 62 . . . housing,
22a . . . supporting section,
23 . . . cover bulging portion,
24 . . . housing bulging portion,
30, 100 . . . microneedle,
31, 110, 120 . . . base,
31a, 110a, 120a . . . projection forming surface,
31b, 110b, 120b . . . supported surface,
31a1, 110c . . . abutted section,
31a2, 102 . . . projection forming section,
32, 101 . . . projection,
33 . . . notch,
41 . . . cover opening end,
42 . . . abutment surface,
43 . . . abutment side surface,
44 . . . cover facing surface,
45 . . . facing side surface,
46, 77 . . . close-contact section,
47, 57, 103a . . . opening,
48 . . . contact surface,
49 . . . opening side surface,
51, 55 . . . housing facing surface,
52 . . . housing opening end,
53 . . . supporting surface,
54 . . . supporting side surface,
56 . . . housing side surface,
61a, 92, 94 . . . cover protruding member,
61s . . . cover outer surface,
61a1 . . . first cover protruding member,
61a2 . . . second cover protruding member,
62a, 91, 93, 96, 98 . . . housing protruding member,
62s . . . housing outer surface,
62a1 . . . first housing protruding member,
62a2 . . . second housing protruding member,
71 . . . cover tubular body,
72 . . . cover bottom,
73 . . . cover tubular end,
74 . . . bottom contact section,
75 . . . elastic mechanism,
76 . . . base contact section,
81 . . . housing tubular body,
82 . . . housing bottom,
83 . . . housing tubular end,
95, 97 . . . spaced section,
101a . . . distal end,
102a . . . forming surface,
103 . . . adhesive sheet,
104 . . . adhesive layer,
105 . . . base sheet,
106 . . . peeling sheet Obviously, numerous modifications and variations of the present invention are possible in light of the above teachings. It is therefore to be understood that within the scope of the appended claims, the invention may be practiced otherwise than as specifically described herein.

What is claimed is:

1. A microneedle unit, comprising:
a microneedle; and
a microneedle container having a housing that houses the microneedle and a cover that covers the microneedle housed in thy: housing,
wherein the microneedle includes a base and a projection formed on a first surface of the base such that the base has a second surface supported by a supporting portion of the housing in the microneedle container and that the base has an abutted portion, the cover has an abutment portion that faces the abutted portion of the base, and a facing portion that faces the projection of the microneedle, the base and the cover are configured such that a distance between the abutment portion of the cover and the facing portion of the cover is larger than a distance between the abutted portion of the base and a distal end of the projection in an extending direction in which the projection projects from the first surface of the base, and that a distance between the abutment portion of the cover and the supporting portion of the housing in the microneedle container is smaller than a sum of a distance between the abutted portion of the base and the second surface of the base and a distance between the abutted portion of the base and the distal end of the projection of the microneedle in the extending direction, the cover has a tubular body having an open end portion and a closed end portion closed with a cover bottom in a sheet form, the cover includes a cover protruding member which extends from the cover bottom toward the open end portion of the tubular body such that the abutment portion is formed on a distal end of the cover protruding member, the housing has a tubular body having an open end portion and a closed end portion closed with a housing bottom in a sheet form, the housing includes a housing protruding member which extends from the housing bottom toward the open end portion of the housing, the supporting portion is formed on a distal end of the housing protruding member, the cover and the housing satisfy (L1+L2)<(M1+M2), where L1 is a cover length from an inner surface of the cover bottom to the open end portion of the cover, M1 is a cover protruding member length from the cover bottom to the distal end of the cover protruding member, L2 is a housing length from an inner surface of the housing bottom to the open end portion of the housing, and M2 is a housing protruding member length from the housing bottom to the distal end of the housing protruding member, each of the cover and the housing includes an opening and a contact portion that surrounds the opening, at least one of the cover protruding member and the housing protruding member comprises an elastic member configured to change a length in the extending direction, and the elastic member has an elastic portion having elasticity higher than elasticity of a portion of the elastic member other than the elastic portion.

2. The microneedle unit of claim 1, wherein the abutment portion of the cover has an adhesive strength different from an adhesive strength of the supporting portion adhered to the base.

3. The microneedle unit of claim 2, wherein each of the cover and the housing has a contact portion that surrounds the opening such that the contact portion of the cover makes contact with the contact portion of the housing, and one of the abutment portion and the supporting portion forms an adhered portion adhered to the base with an adhesive strength greater than an adhesive strength between the base and the other one of the abutment portion and the supporting portion.

4. The microneedle unit of claim 3, wherein the microneedle includes the projection formed in a plurality on the first surface of the base.

5. The microneedle unit of claim 2, wherein the microneedle includes the projection formed in a plurality on the first surface of the base.

6. The microneedle unit of claim 1, wherein the elastic portion comprises a spring.

7. The microneedle unit of claim 6, wherein the abutment portion of the cover has an adhesive strength different from an adhesive strength of the supporting portion adhered to the base.

8. The microneedle unit of claim 7, wherein the housing has a contact portion that surrounds the opening such that the cover makes contact with the contact portion of the housing, and one of the abutment portion and the supporting portion forms an adhered portion adhered to the base with an adhesive strength greater than an adhesive strength between the base and the other one of the abutment portion and the supporting portion.

9. The microneedle unit of claim 7, wherein the microneedle includes the projection formed in a plurality on the first surface of the base.

10. The microneedle unit of claim 1, wherein each of the cover and the housing comprises the elastic member.

11. The microneedle unit of claim 10, wherein the elastic portion comprises a spring.

12. The microneedle unit of claim 11, wherein the abutment portion of the cover has an adhesive strength different from an adhesive strength of the supporting portion adhered to the base.

13. The microneedle unit of claim 10, wherein the abutment portion of the cover has an adhesive strength different from an adhesive strength of the supporting portion adhered to the base.

14. The microneedle unit of claim 1, wherein the housing protruding member comprises the elastic member and is formed in a plurality at corner portions of the housing bottom.

15. The microneedle unit of claim 14, wherein the elastic portion comprises a spring.

16. The microneedle unit of claim 14, wherein the microneedle includes the projection formed in a plurality on the first surface of the base.

17. The microneedle unit of claim 14, wherein the abutment portion of the cover has an adhesive strength different from an adhesive strength of the supporting portion adhered to the base.

18. The microneedle unit of claim 1, wherein the cover protruding member comprises the elastic member and is formed in a plurality at corner portions of the cover bottom.

19. The microneedle unit of claim 1, wherein the microneedle includes the projection formed in a plurality on the first surface of the base.

20. A microneedle container, comprising:
a container body including a housing configured to house a microneedle and a cover configured to cover the microneedle,
wherein the microneedle includes a base and a projection formed on a first surface of the base such that the base has a second surface supported by a supporting portion of the housing in the microneedle container and that the base has an abutted portion, the cover has an abutment portion positioned to face the abutted portion of the microneedle, and a facing portion positioned to face the projection of the microneedle, the cover is configured such that a distance between the abutment portion and the facing portion is larger than a distance between the abutted portion of the base and a distal end of the projection in an extending direction in which the projection projects from the first surface of the base and that a distance between the abutment portion of the cover and the supporting portion of the housing in the microneedle container is smaller than a sum of a distance between the abutted portion of the base and the second surface of the base and a distance between the abutted portion of the base and the distal end of the projection of the microneedle in the extending direction, the cover has a tubular body having an open end portion and a closed end portion closed with a cover bottom in a sheet form, the cover includes a cover protruding member which extends from the cover bottom toward the open end portion of the tubular body such that the abutment portion is formed on a distal end of the cover protruding member, the housing has a tubular body having an open end portion and a closed end portion closed with a housing bottom in a sheet form, the housing includes a housing protruding member which extends from the housing bottom toward the open end portion of the housing, the supporting portion is formed on a distal end of the housing protruding member, the cover and the housing satisfy (L1+L2)<(M1+M2), where L1 is a cover length from an inner surface of the cover bottom to the open end portion of the cover, M1 is a cover protruding member length from the cover bottom to the distal end of the cover protruding member, L2 is a housing length from an inner surface of the housing bottom to the open end portion of the housing, and M2 is a housing protruding member length from the housing bottom to the distal end of the housing protruding member, each of the cover and the housing includes an opening and a contact portion that surrounds the opening, at least one of the cover protruding member and the housing protruding member comprises an elastic member configured to change a length in the extending direction, and the elastic member has an elastic portion having elasticity higher than elasticity of a portion of the elastic member other than the elastic portion.

* * * * *